(12) United States Patent
Al Barazi et al.

(10) Patent No.: US 11,103,267 B2
(45) Date of Patent: Aug. 31, 2021

(54) SURGICAL FORCEPS AND METHODS OF USE

(71) Applicant: American University of Beirut, Beirut (LB)

(72) Inventors: Randa Al Barazi, Beirut (LB); Elie Shammas, San Diego, CA (US)

(73) Assignee: American University of Beirut, Beirut (LB)

( * ) Notice: Subject to any disclaimer, the term of this patent is extended or adjusted under 35 U.S.C. 154(b) by 100 days.

(21) Appl. No.: 16/717,380

(22) Filed: Dec. 17, 2019

(65) Prior Publication Data

US 2020/0187968 A1 Jun. 18, 2020

Related U.S. Application Data

(60) Provisional application No. 62/781,245, filed on Dec. 18, 2018.

(51) Int. Cl.
*A61B 17/29* (2006.01)
*A61B 17/28* (2006.01)

(52) U.S. Cl.
CPC .......... *A61B 17/29* (2013.01); *A61B 17/2804* (2013.01); *A61B 2017/2941* (2013.01); *A61B 2017/2947* (2013.01)

(58) Field of Classification Search
CPC .............. A61B 17/282; A61B 17/2816; A61B 17/2812; A61B 17/2804; A61B 17/28; A61B 17/29; A61B 17/50; A61B 2017/2939; A61B 2017/2936; A61B 2017/2933; A61B 2017/2932; A61B 2017/2926; A61B 2017/2924; A61B 2017/2912; A61B 2017/2919; A61B 2017/2922; A61B 2017/2934; A61B 2017/2916; A61B 2017/2915; A61B 2017/2913; A61B 2017/2941; A61B 2017/294; A61B 2017/2947

See application file for complete search history.

(56) References Cited

U.S. PATENT DOCUMENTS

| | | | |
|---|---|---|---|
| 6,361,534 B1 * | 3/2002 | Chen | A61B 17/2804 606/170 |
| 7,875,028 B2 * | 1/2011 | Christian | A61B 18/1492 606/51 |
| 8,568,443 B1 * | 10/2013 | Jackman | A61B 17/00 606/205 |
| 9,168,050 B1 * | 10/2015 | Peine | A61B 17/29 |
| 10,238,493 B1 * | 3/2019 | Metchik | A61B 17/122 |
| 2004/0254607 A1 * | 12/2004 | Wittenberger | A61B 18/02 606/205 |
| 2005/0165429 A1 * | 7/2005 | Douglas | A61B 17/122 606/157 |

FOREIGN PATENT DOCUMENTS

| | | | | |
|---|---|---|---|---|
| AU | 2008249212 A1 * | 6/2009 | | A61B 10/06 |
| CA | 2680258 A1 * | 9/2008 | | A61B 17/29 |
| DE | 19719090 A1 * | 11/1998 | | A61B 17/29 |
| WO | WO-03013374 A1 * | 2/2003 | | A61B 17/29 |

\* cited by examiner

*Primary Examiner* — Tan-Uyen T Ho
*Assistant Examiner* — Arwa Mostafa
(74) *Attorney, Agent, or Firm* — Amin Talati Wasserman LLP; J. Peter Paredes

(57) ABSTRACT

Provided herein are systems, methods and apparatuses for surgical forceps for an easier and safer retrieval of foreign bodies in passages for better quality of care for patients.

5 Claims, 22 Drawing Sheets

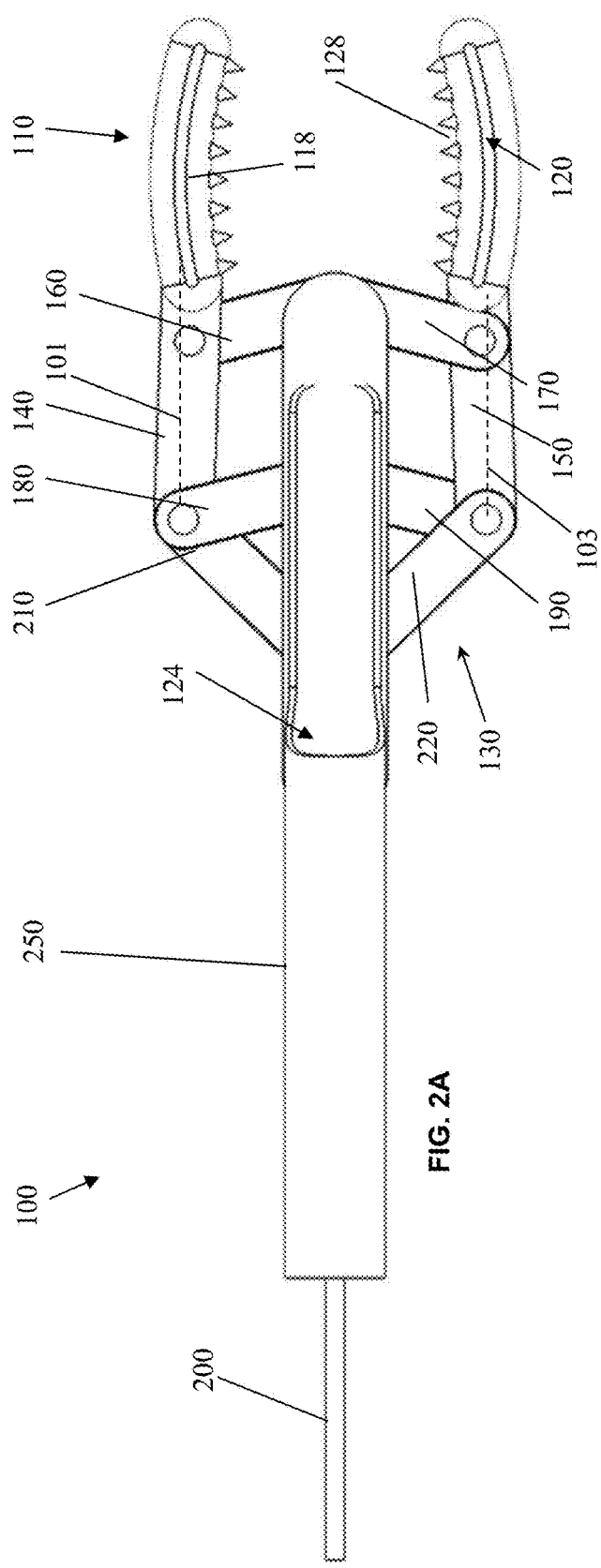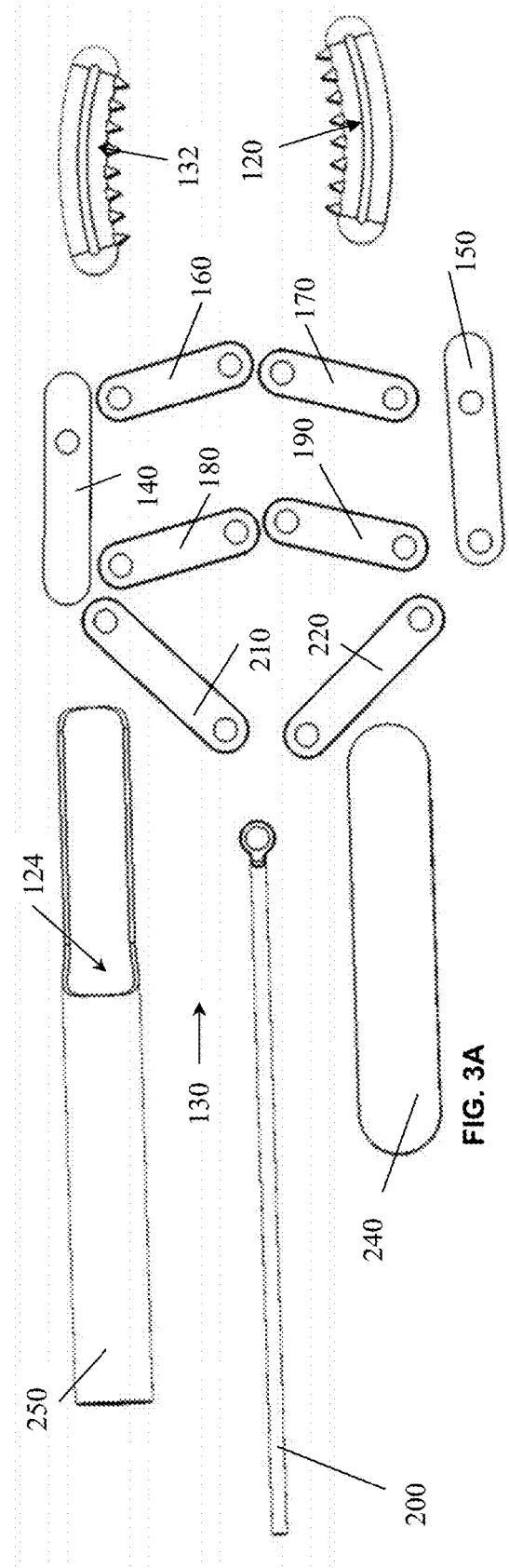

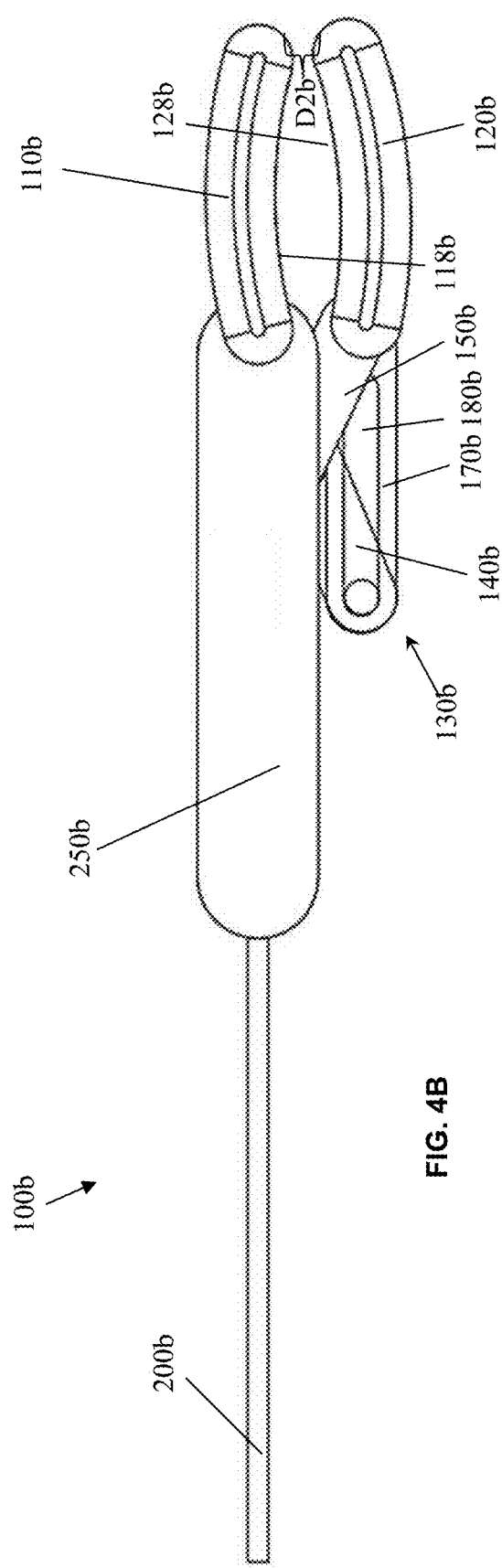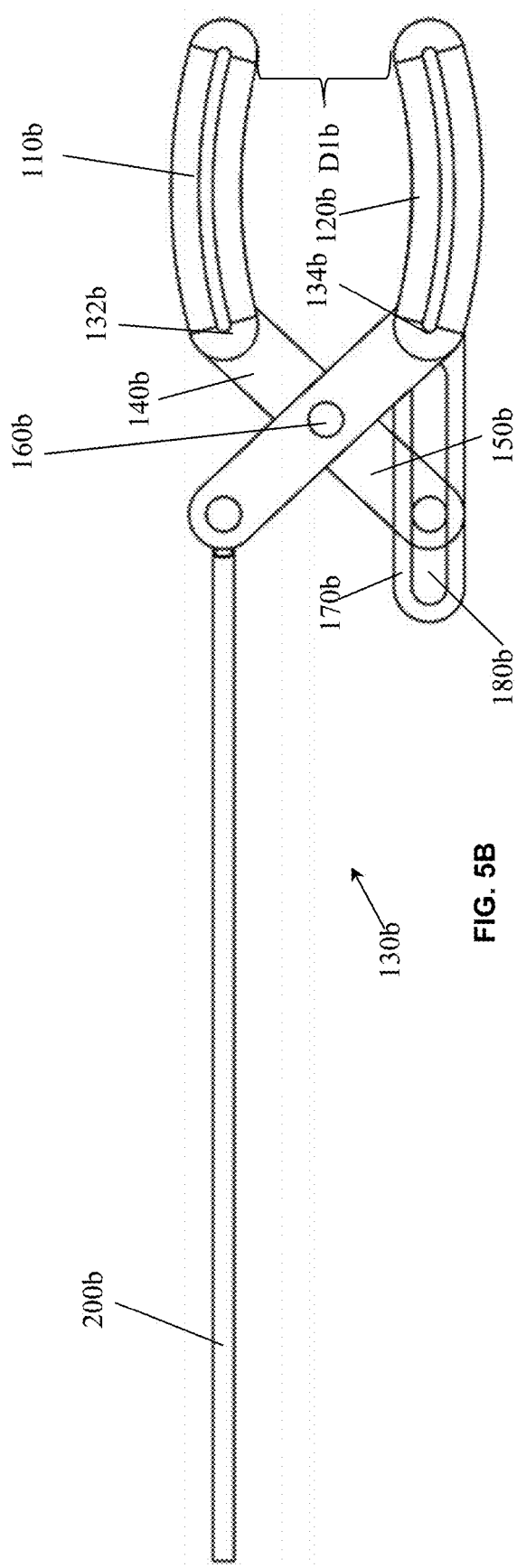
FIG. 4B
FIG. 5B

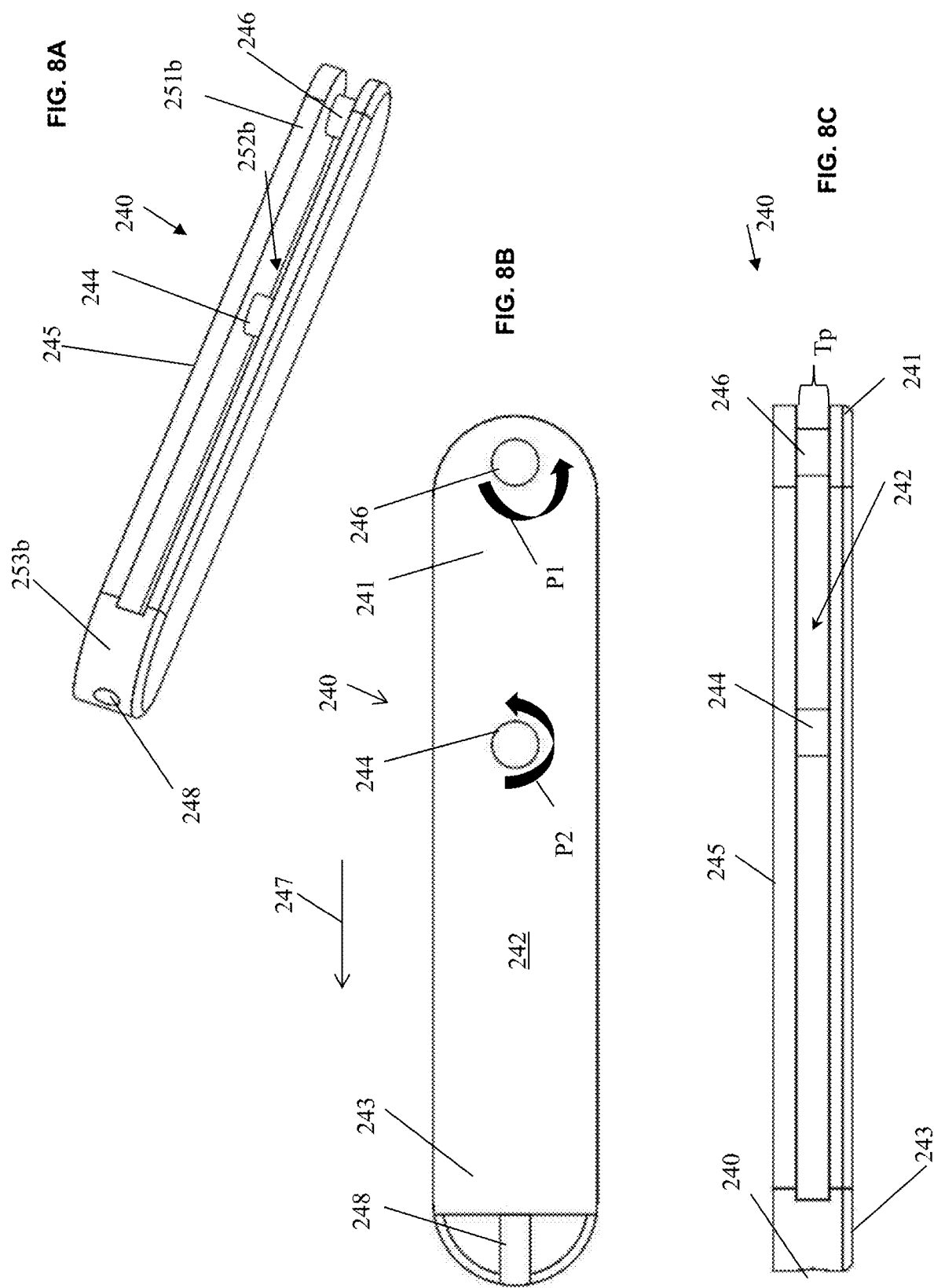

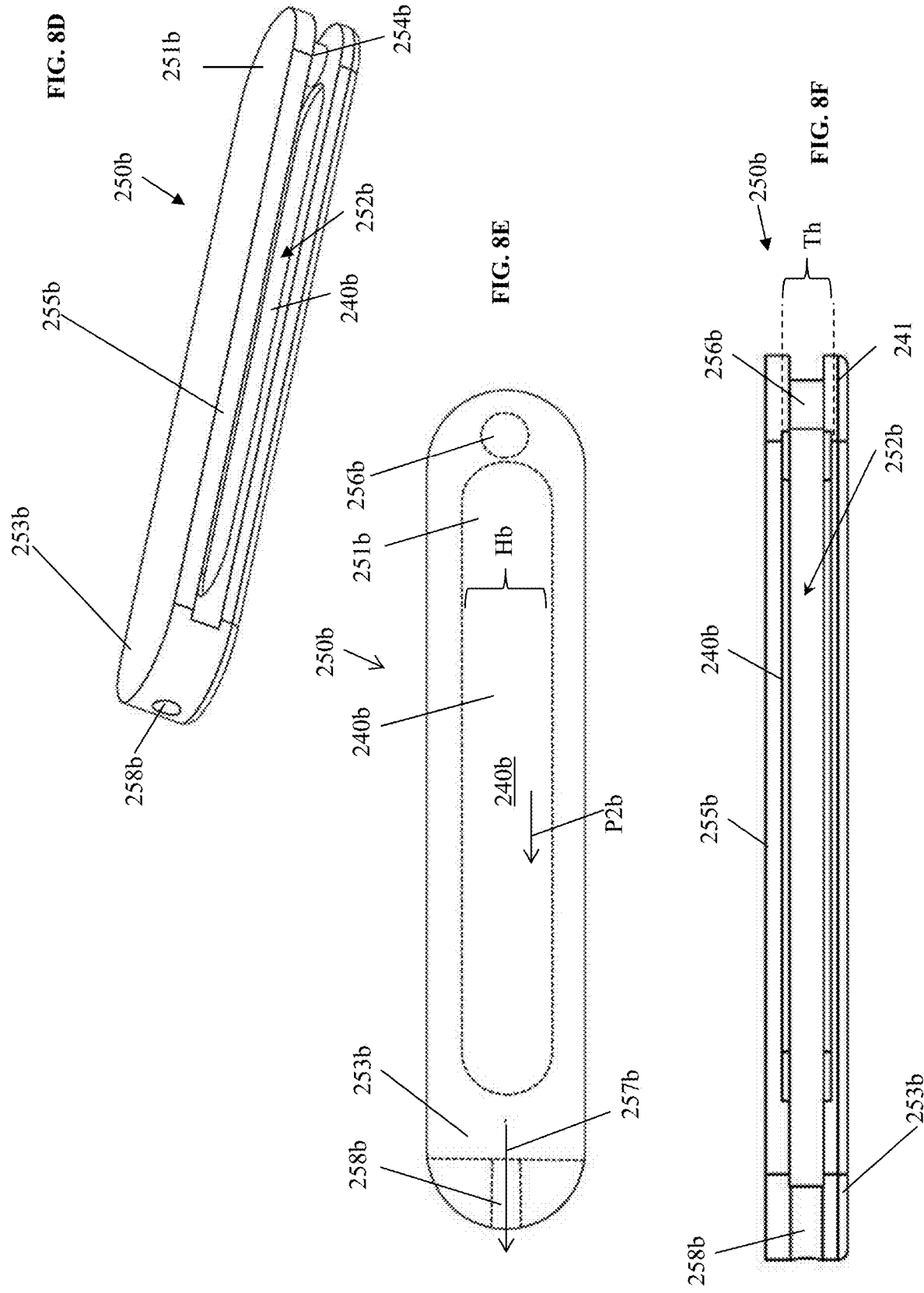

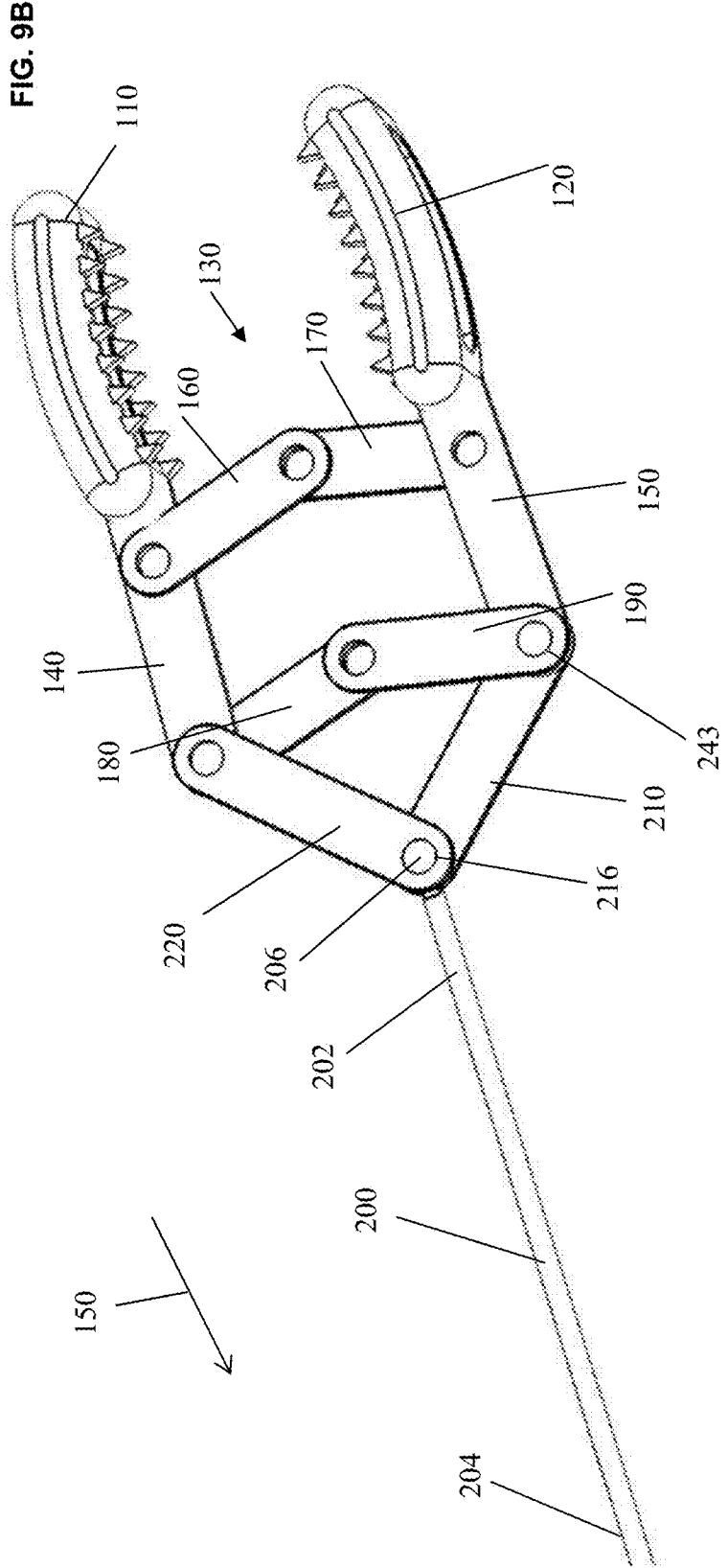

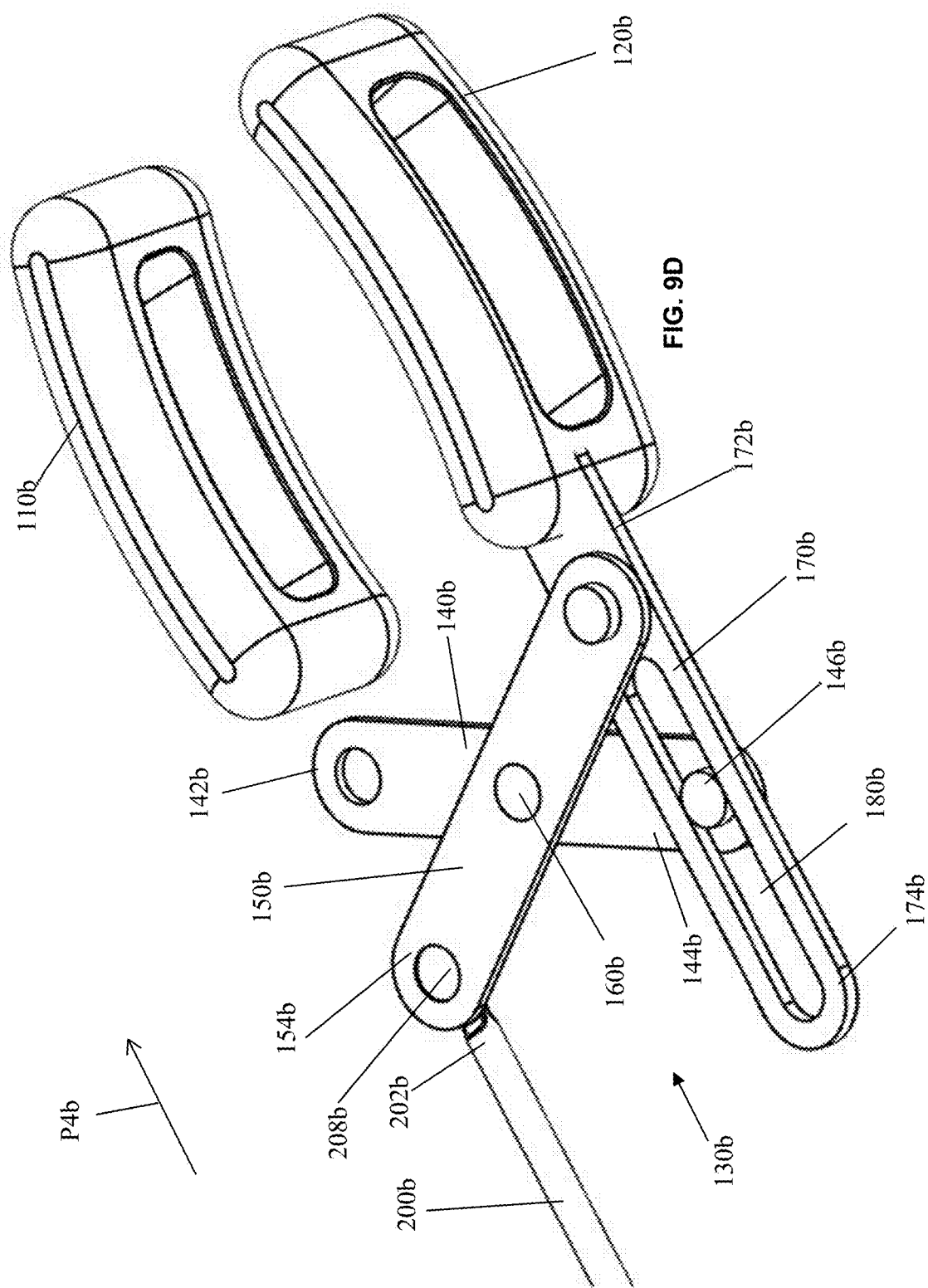

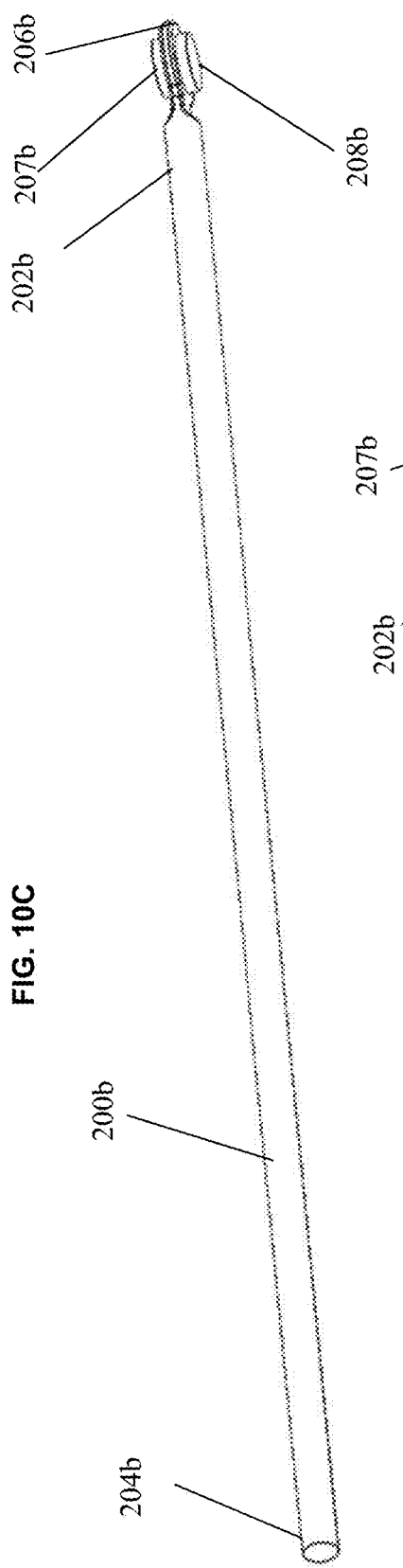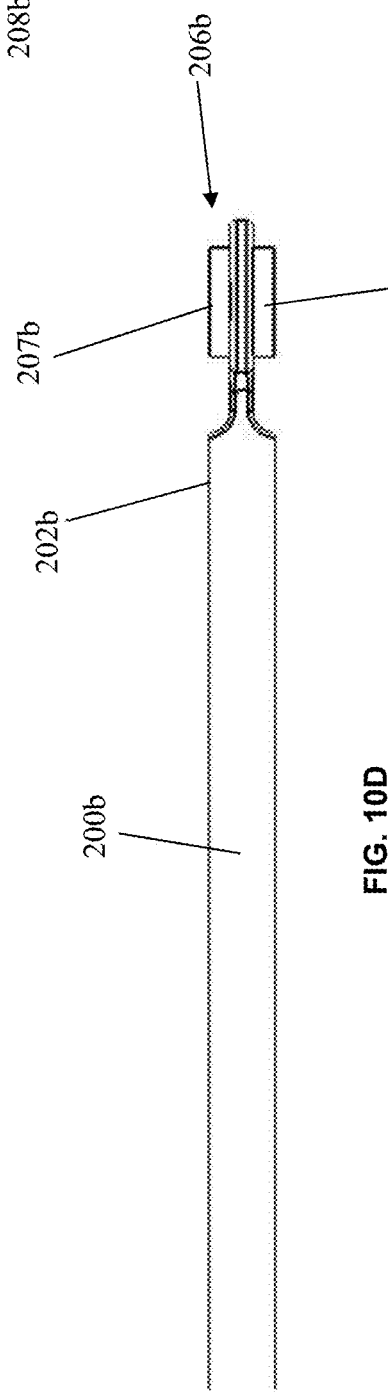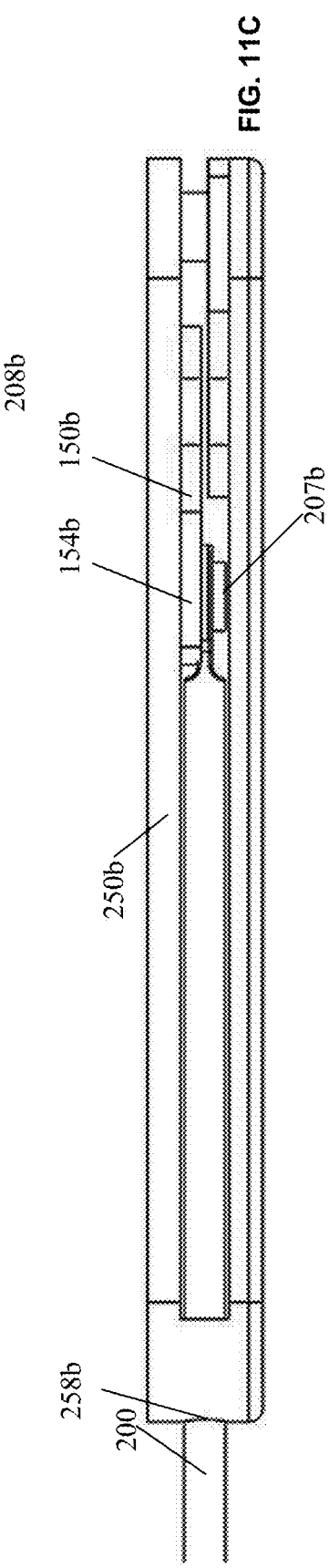

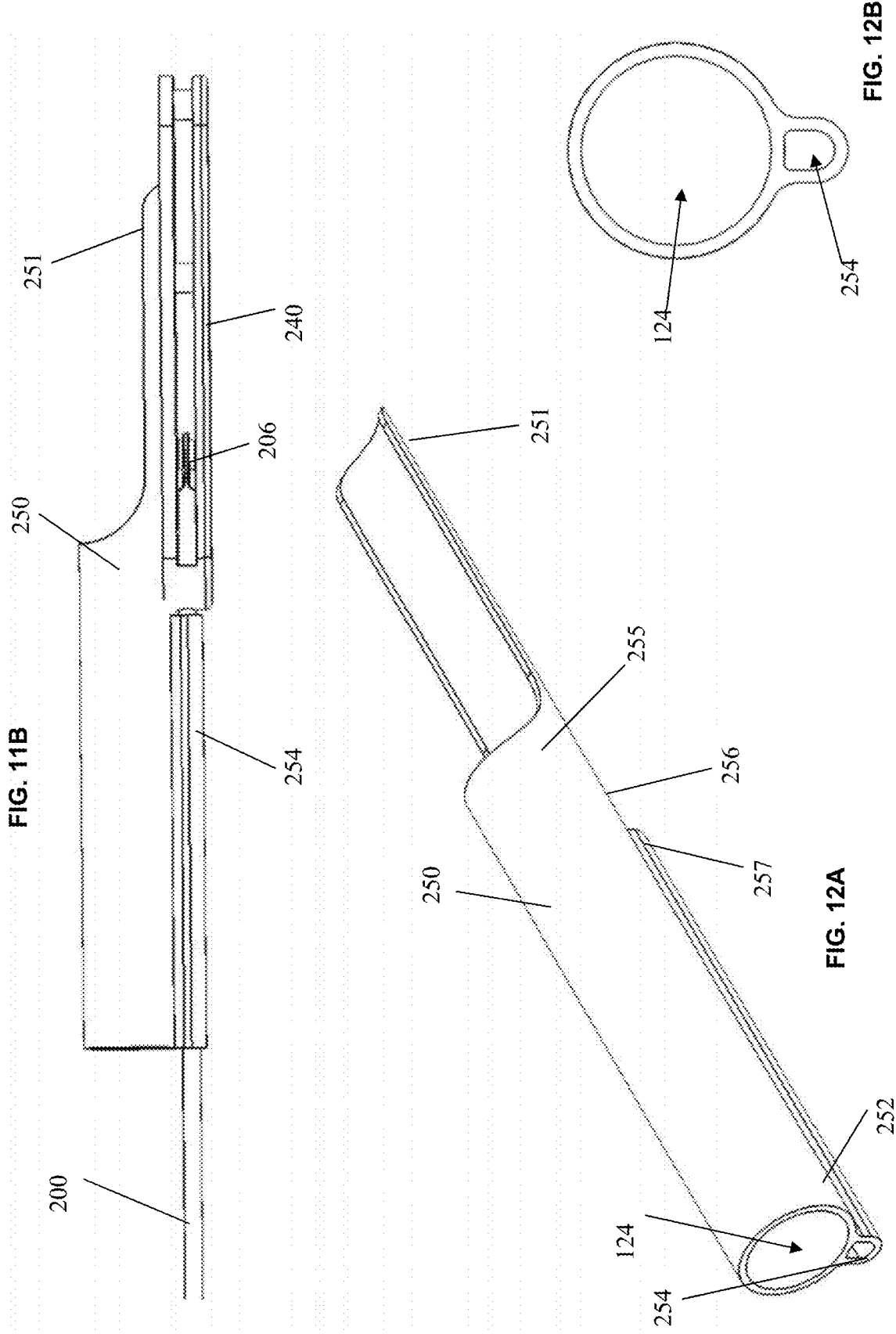

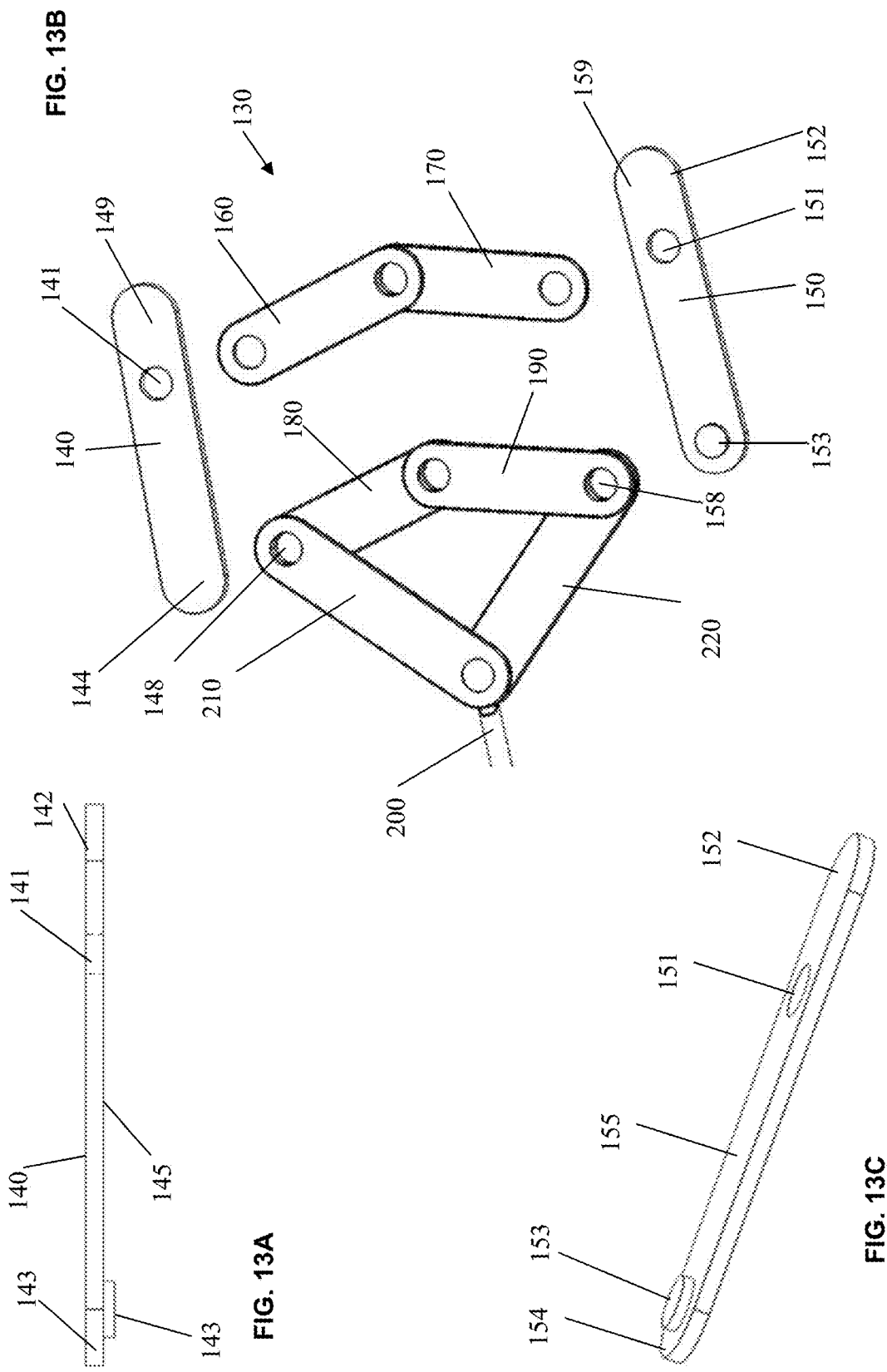

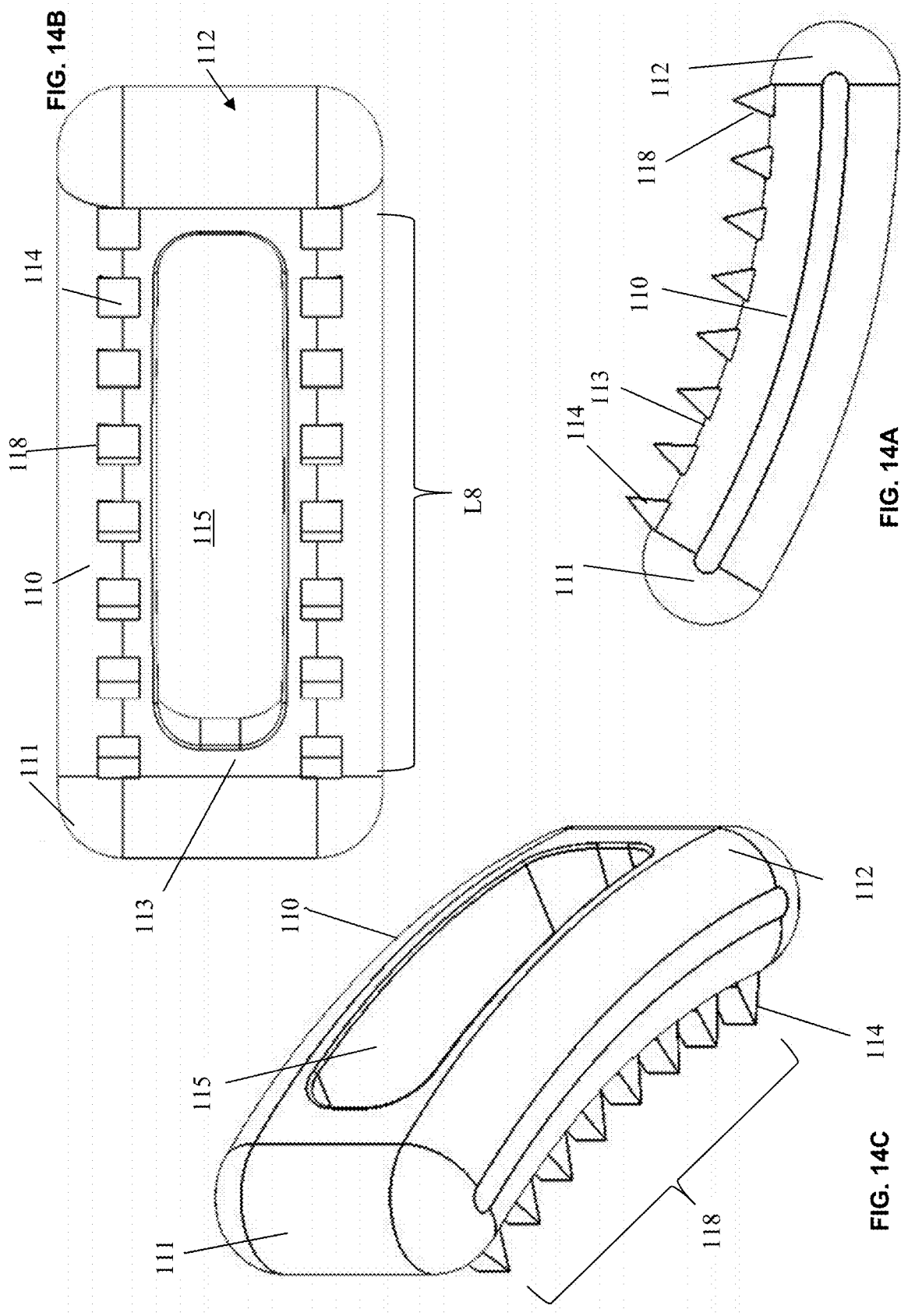

SURGICAL FORCEPS AND METHODS OF USE

CROSS-REFERENCE TO RELATED APPLICATIONS

The present application claims priority to U.S. provisional application Ser. No. 62/781,245, filed Dec. 18, 2018, herein incorporated by reference in its entirety.

BACKGROUND

The invention generally relates to surgical instruments.

Aerodigestive foreign bodies are an emergency which need intervention as soon as possible. Multiple forceps exist to extract foreign bodies but the most challenging foreign bodies are the smooth rounded foreign bodies which are difficult to grasp with the current forceps in the market. With the current forceps, such foreign bodies can slip distally into the airway. The only instrument available for such foreign bodies are baskets which need 2 persons to handle, it can break easily and need expertise. Easier and safer retrieval of certain foreign bodies in the airway and esophagus leading to better quality of care for patients. The present invention solves these problems, as well as others.

SUMMARY OF THE INVENTION

Provided herein are systems, methods and apparatuses for a Bronchoscopy Forceps.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2A is a side view of the surgical forceps according one embodiment.

FIG. 3A is an exploded view of the surgical forceps according one embodiment.

FIG. 4B is a side view of the closed position of an alternative embodiment of the surgical forceps.

FIG. 5B is a side view of an alternative embodiment of the surgical forceps showing the three-bar mechanism without the pivot housing.

FIG. 8A is perspective view of the pivot housing according one embodiment; FIG. 8B is a top view of the pivot housing according one embodiment; FIG. 8C is a side view of the pivot housing according to one embodiment; FIG. 8D is perspective view of the pivot housing according to an alternative embodiment; FIG. 8E is a top view of the pivot housing according to an alternative; FIG. 8F is a side view of the pivot housing according to an alternative embodiment.

FIG. 9B is a perspective view of the four-bar mechanism coupled with the actuator rod without the pivot housing; FIG. 9D is a perspective view of the three-bar mechanism coupled with the actuator rod without the pivot housing.

FIG. 10C is a perspective view of the actuator rod according to one embodiment; and FIG. 10D is a side view of the actuator rod according to one embodiment.

FIG. 11B is a side view of the pivot housing coupled with the actuator rod and the tube according to one embodiment; FIG. 11C is a side view of the actuator rod coupled to the second cross link and the pivot housing.

FIG. 12A is a perspective view of the central tube according to one embodiment; FIG. 12B is a back view of the central tube according to one embodiment.

FIG. 13A is a side view of the first jaw according to one embodiment; FIG. 13B is an exploded view of the four-bar mechanism with the first jaw and second jaw separated; FIG. 13C is a perspective view of the second jaw according one embodiment.

FIG. 14A is a perspective view of the first clamp according to one embodiment; FIG. 14B is a bottom view of the first clamp according to one embodiment; and FIG. 14C is a side view of the first clamp according to one embodiment.

DETAILED DESCRIPTION OF THE INVENTION

Figure 1A:
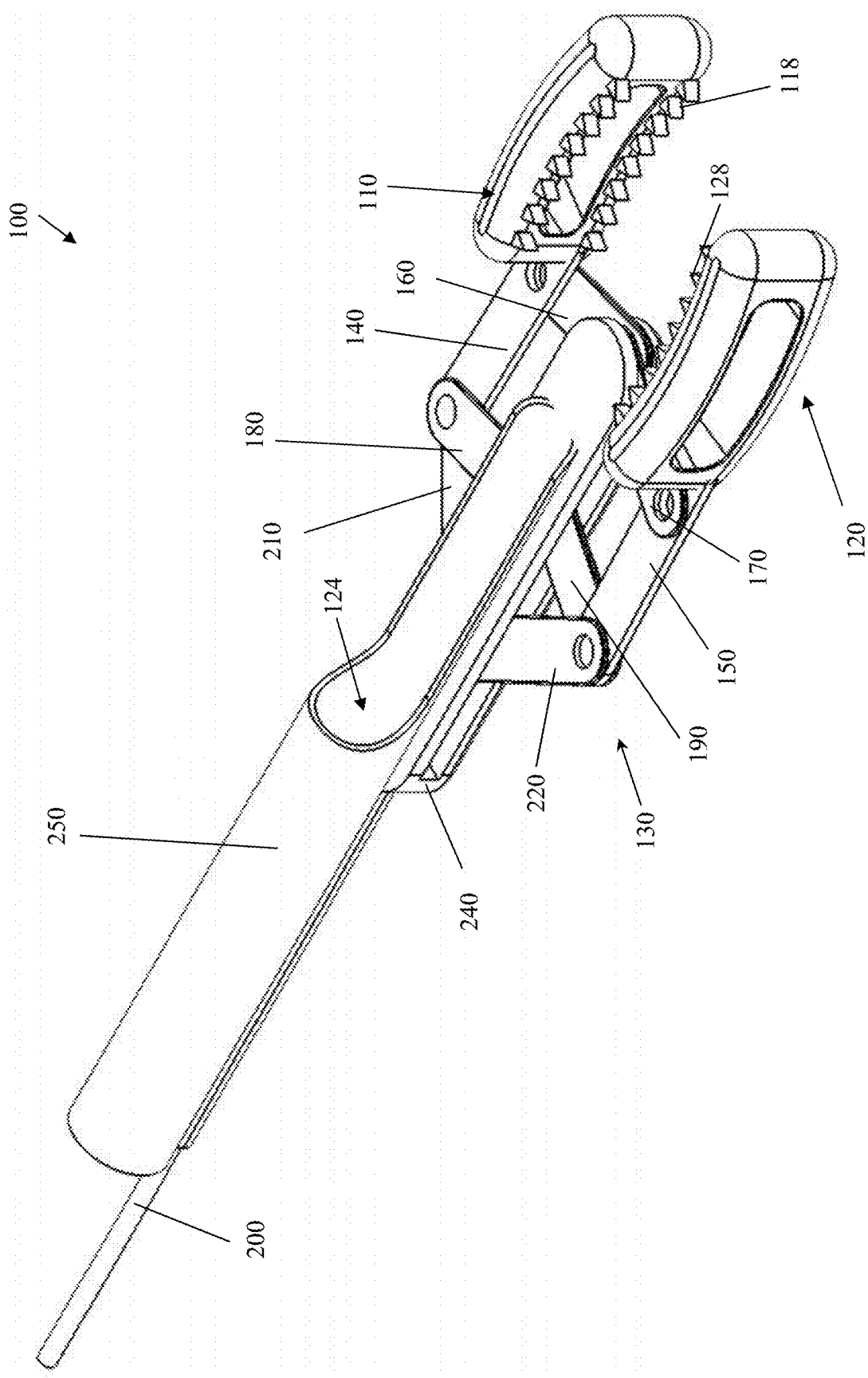
FIG. 1A is a perspective view of the surgical forceps according one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, and the word "nearly" is to be construed as indicating a deviation of up to and inclusive of 10% from the stated numerical value or an estimated position state. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The words proximal and distal are applied herein to denote specific ends of components of the surgical forceps described herein. A proximal end refers to the end of the surgical forceps nearer to an operator of the instrument when the surgical forceps is being used. A distal end refers to the end of a component further from the operator and extending towards the surgical area of a patient.

The surgical forceps provides direct, quicker and safer retrieval of certain foreign bodies. The mechanism of this forceps allows total grasp of certain foreign bodies without slipping. The surgical forceps solves the problem of slippery, rounded foreign bodies. In one embodiment, the surgical forceps are used in bronchoscopy; however, the surgical forceps may be used in other surgical procedures as determined by one of ordinary skill in the art.

Figure 3B:
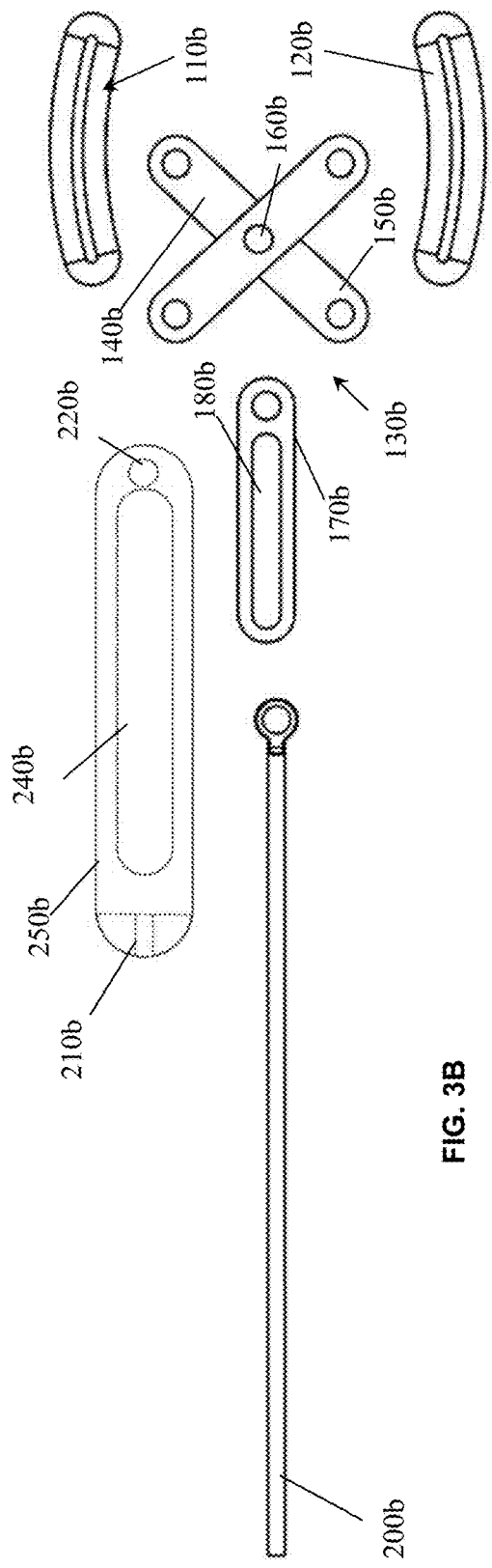
FIG. 3B is an exploded view of an alternative embodiment of the surgical forceps.
Figure 4A:
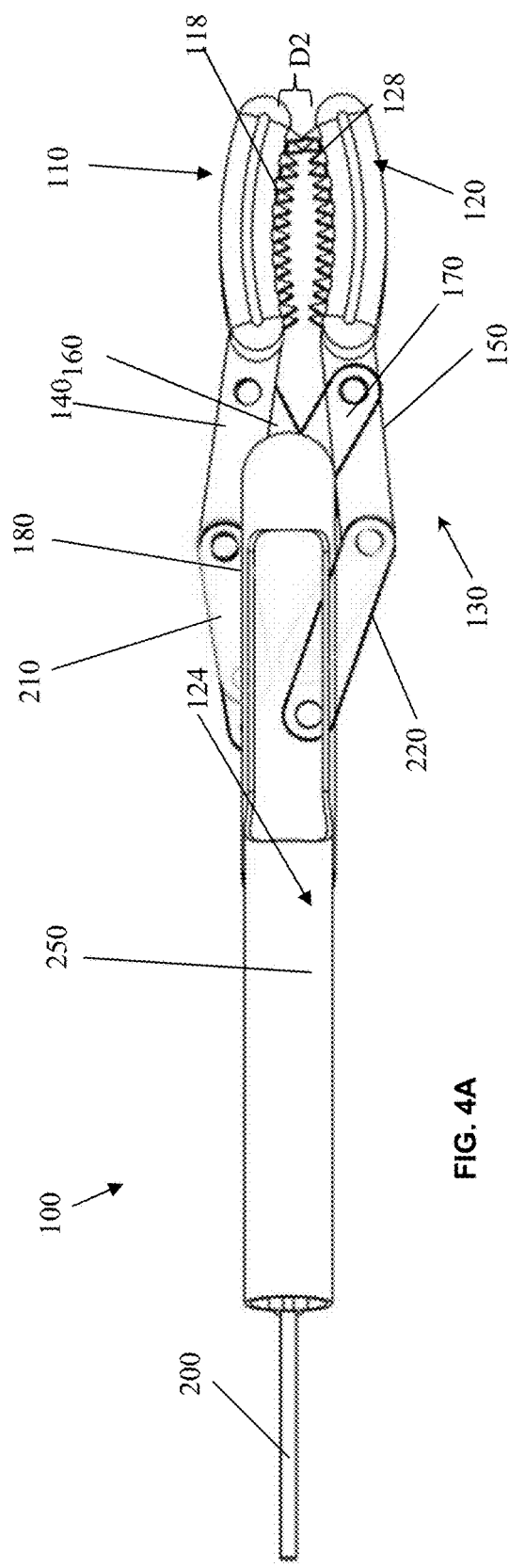
FIG. 4A is a side view of the closed position of the surgical forceps according one embodiment.
Figure 5A:
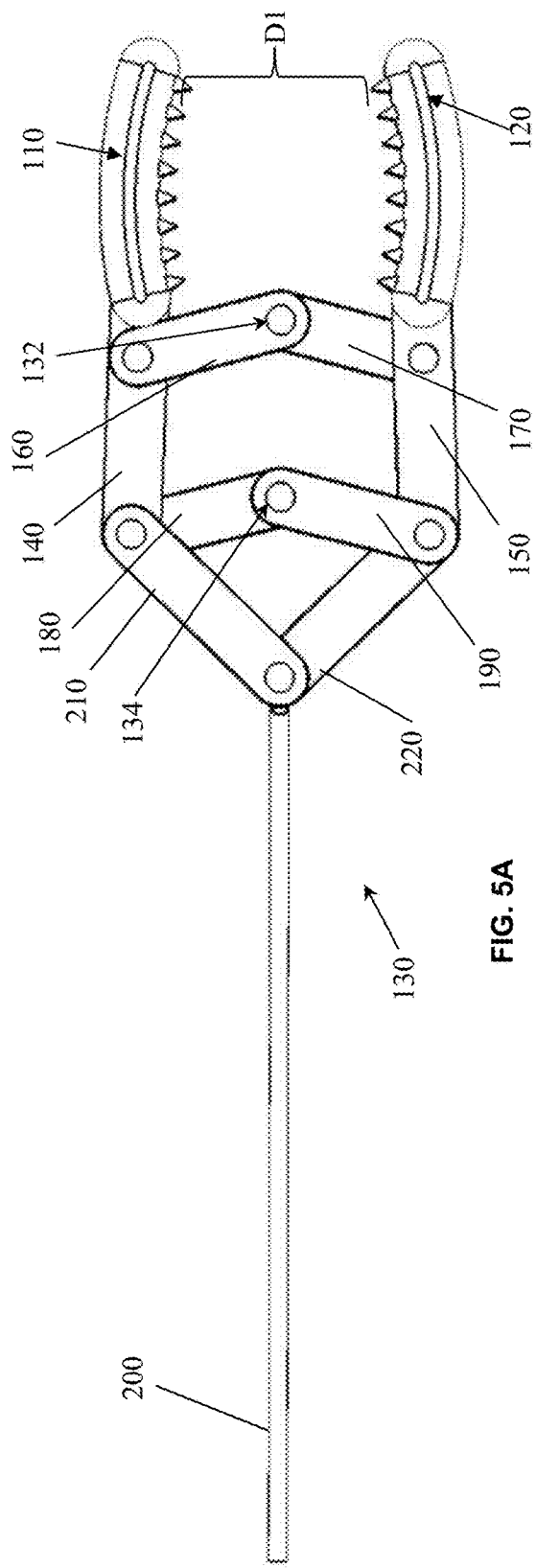
FIG. 5A is a side view of the surgical forceps showing the four-bar mechanism without the pivot housing and central tube according one embodiment.

As shown in FIGS. 1A, 2A, and 3A, the surgical forceps 100 comprise a first clamp 110 and a second clamp 120 operably coupled to a four-bar mechanism 130 to move the first clamp 110 and the second clamp 120 from a nearly parallel open position to a nearly parallel closed position, as shown in FIGS. 4*a* and 5A. The four-bar mechanism 130 comprises a first jaw 140 operably coupled to the first clamp 110 and a second jaw 150 operably coupled to the second clamp 120. The first jaw 140 includes a first longitudinal axis 101 and the second jaw 150 includes a second longitudinal axis 103, as shown in FIG. 2A. The four-bar mechanism 130 keeps the first longitudinal axis 101 of the first jaw 140 parallel or nearly parallel relative to the second longitudinal axis 103 of the second jaw 150. The nearly parallel can be realized by modifying the lengths of some links, as described below. The four-bar mechanism 130 moves the virtual pivot point of the jaws to achieve perfectly parallel jaws or to relatively very far points to achieve nearly parallel jaws. The first clamp 110 includes a first gripping portion 118 and the second clamp 120 includes a second gripping portion 128 in which to grip a foreign body when the surgical forceps 100 are in the parallel or nearly parallel closed position. The first jaw 140 is operably attached to a first front link 160 and a first back link 180 and the second jaw 150 is operably attached to a second front link 170 and a second back link 190. The first jaw 140 and second jaw 150 are operably coupled to an actuator rod 200 which moves the first jaw 140 and the second jaw 150 through a first linking actuator 210 and a second linking actuator 220 by a double pivot action. A central tube 250 is operably coupled to the actuator rod 200 and holds a pivot housing 240 to maintain and house the four-bar mechanism 130. The central tube 250 includes an opening 124 through which a camera or viewing mechanism is coaxially disposed for viewing the distal end of the surgical forceps 100.

Figure 1B:
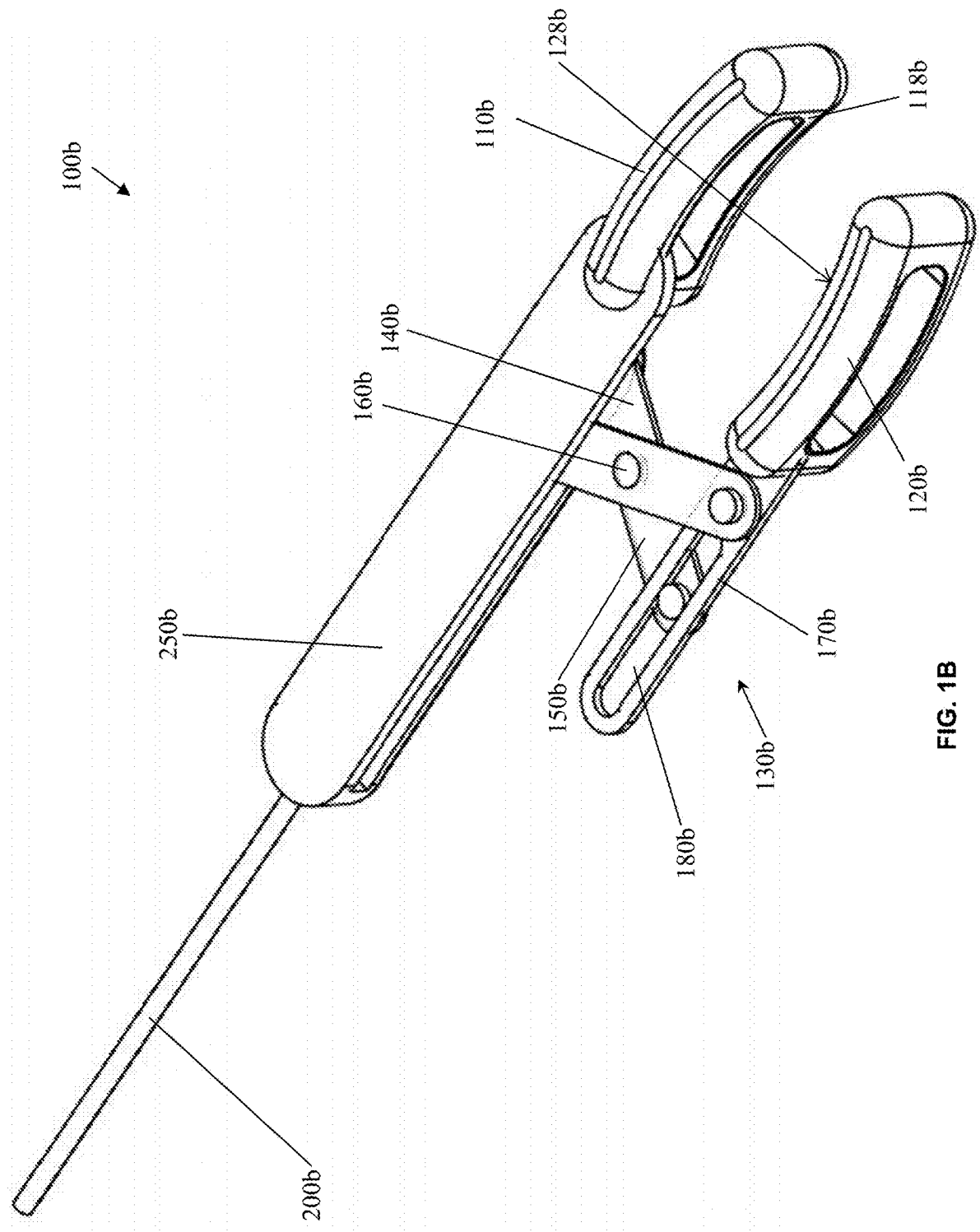
FIG. 1B is a perspective view of an alternative embodiment of the surgical forceps.
Figure 2B:
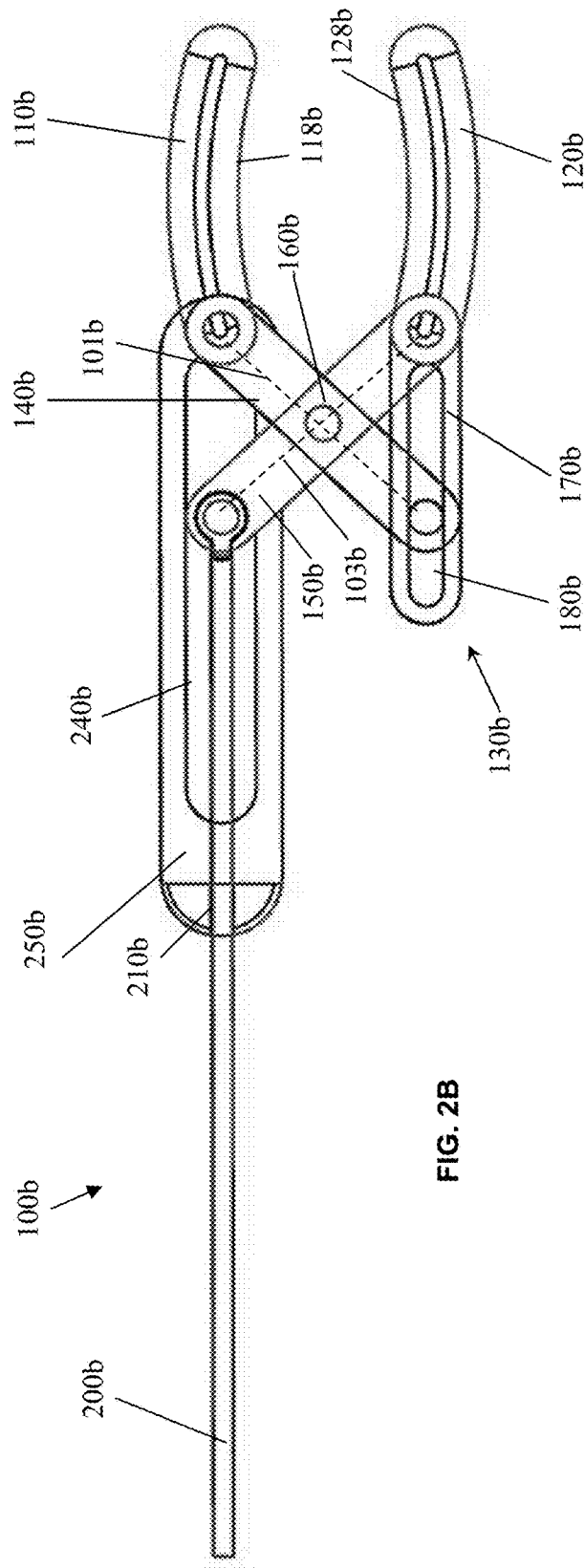
FIG. 2B is a side view of an alternative embodiment of the surgical forceps.

An alternative embodiment of the surgical forceps 100*b* is shown in FIGS. 1B, 2B, 3B, comprises a first clamp 110*b* and a second clamp 120*b* operably coupled to a three-bar mechanism 130*b* to move the first clamp 110*b* towards the second clamp 120*b* from a nearly parallel open position to a nearly parallel closed position, as shown in FIGS. 4B and 5B. The three-bar mechanism 130*b* comprises a first cross-link 140*b* operably coupled to the first clamp 110*b* and a second crosslink 150b operably coupled to the second clamp 120b. The first crosslink 140b includes a first longitudinal axis 101b and the second crosslink 150b includes a second longitudinal axis 103, as shown in FIG. 2B. The three-bar mechanism 130b keeps the first longitudinal axis 101b of the first crosslink 140b perpendicular or nearly perpendicular relative to the second longitudinal axis 103b of the second crosslink 150b. The nearly perpendicular can be realized by modifying the lengths of some links, as described below. The three-bar mechanism 130b moves the virtual pivot point of the clamps to achieve perfectly parallel clamps or to relatively very far points to achieve nearly parallel clamps. The first clamp 110b includes a first gripping portion 118b and the second clamp 120b includes a second gripping portion 128b in which to grip a foreign body when the surgical forceps 100b are in the parallel or nearly parallel closed position. The first crosslink 140b is operably attached to the second crosslink 150b at a central pivot 160b. The first crosslink 140b is operably attached to a pivot link 170b and the second crosslink 150b is operably attached to the pivot link 170b. The pivot link 170b includes a slidable opening 180b through which the first crosslink 140 longitudinally slides to permit the first clamp 110b to close. The first crosslink 140 150b is operably coupled to an actuator rod 200b, which moves second crosslink 150b through a pivot housing 250b. The pivot housing 250b is operably coupled to the first crosslink 140b by way of pivot point 220b, as shown in FIGS. 2B and 3B. The pivot housing 250b houses a longitudinal housing 240b to longitudinally permit the second clamp 120b to move along the longitudinal housing 240b. The pivot housing 250b includes an opening 210b through which the actuator rod 200b longitudinally moves.

Figure 6A:
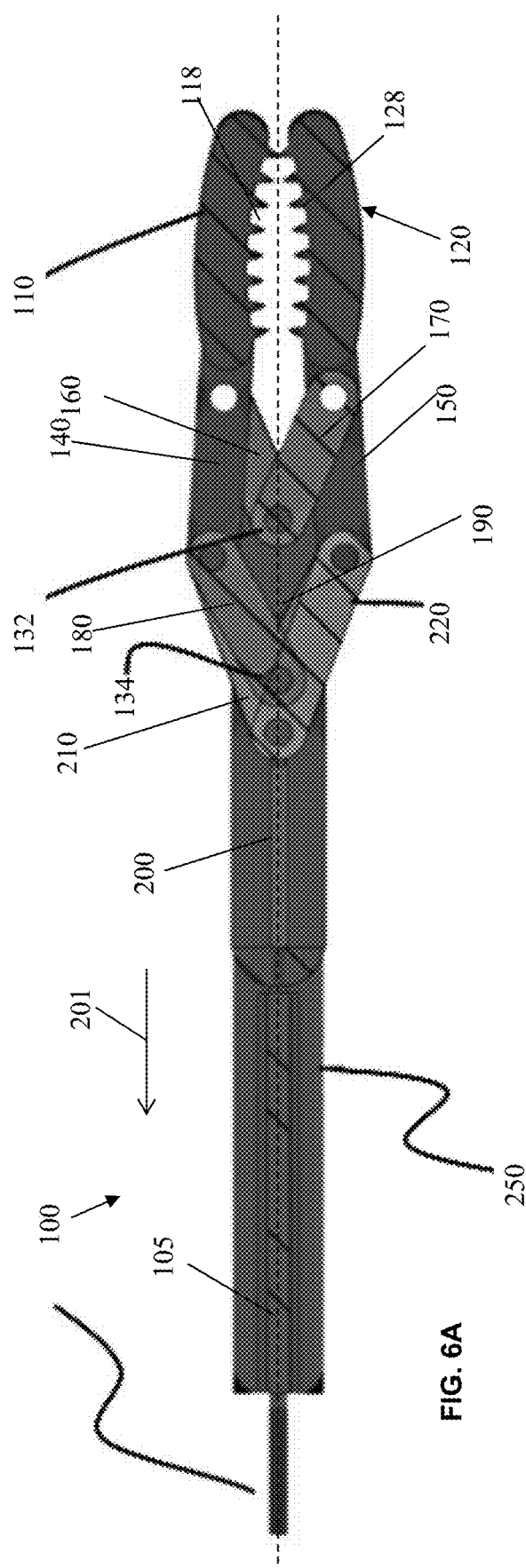
FIG. 6A is a side view surgical forceps in the closed position with the pivot housing and central tube shown in phantom according to one embodiment.
Figure 6B:
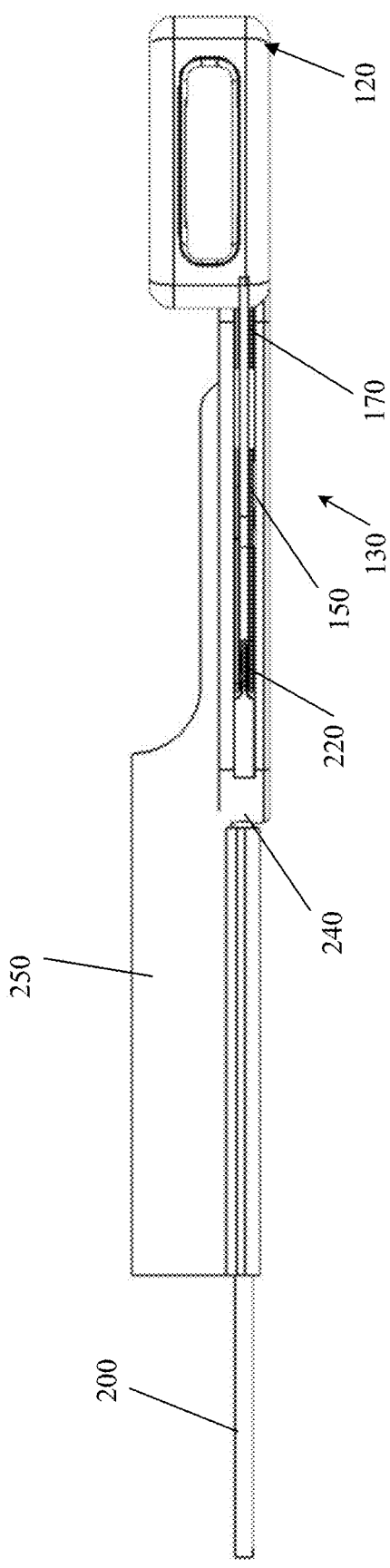
FIG. 6B is a side view surgical forceps in the open position with the pivot housing and central tube according to one embodiment.

As shown in FIG. 5A, the four-bar mechanism 130 keeps the open position and the first clamp and the second clamp separated by distance D1 and moves to the closed position where the first clamp 110 and the second clamp 120 are separated by distance D2, as shown in FIG. 4A. Distance D1 may be between about 1 cm and about 20 cm and distance D2 may be between about 0 cm to about 0.9 cm. The distance D1 and D2 may be altered depending on the type of foreign body being removed. The four-bar mechanism comprises a pivot point 132 between the first front link 160 and the second front link 170, and a second fixed pivot point 134. The actuator rod 200 moves proximally along the longitudinal axis 105 of the surgical forceps 100, generally shown by arrow 201 in FIG. 6A. The actuator rod 200 pulls the first linking actuator 210 and the second linking actuator 220 which then causes the first pivot point 132 and the second fixed pivot point 134 to pivot. The first pivot point 132 closes the first front link 160 and the second front link 170 while the second fixed pivot point 134 closes a first back link 180 and the second back link 190. This closing action closes the first clamp 110 and the second clamp 120 into a parallel or nearly parallel closed position, while the first jaw 140 and the second jaw 150 maintain the first clamp 110 and the second clamp 120 in a parallel or nearly parallel position during the entire time the actuator rod 200 closes the first pivot point 132 and the second fixed pivot point 134. FIG. 6B is a side view surgical forceps in the open position with the pivot housing 240 and central tube 250 according to one embodiment.

Figure 7A:
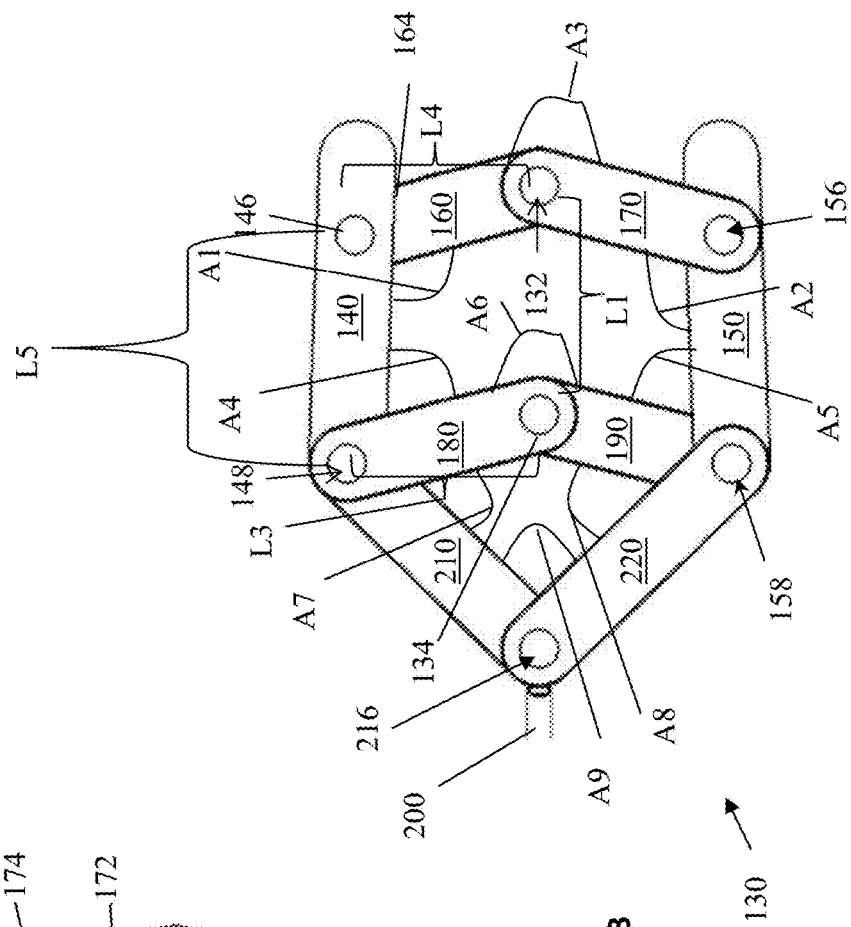
FIG. 7A is a side view of the four-bar mechanism without the pivot housing and central tube according one embodiment.
Figure 7B:
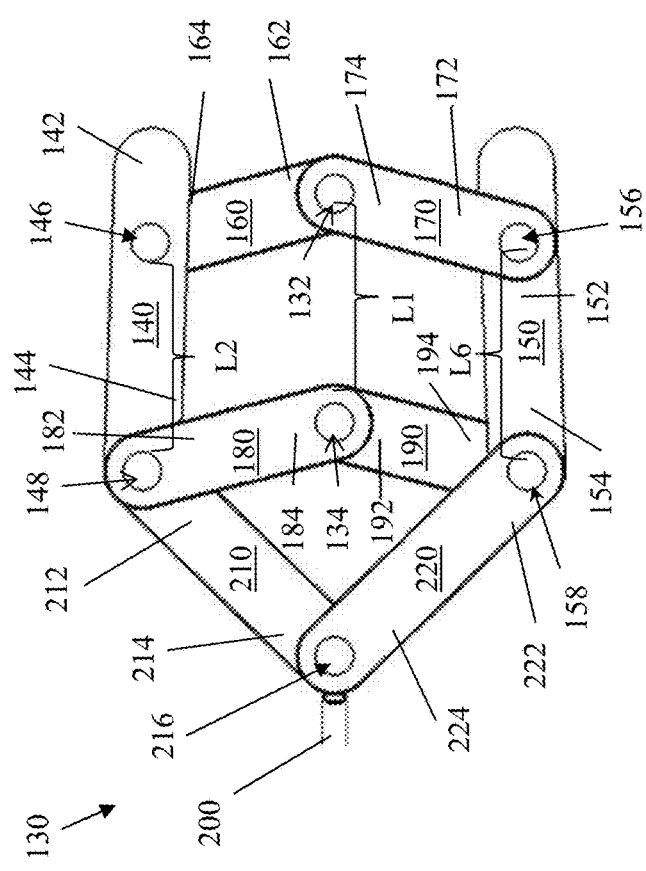
FIG. 7B is a side view of the four-bar mechanism showing the angles A1-A8 without the pivot housing and central tube according one embodiment.

To achieve parallel jaw action of the first longitudinal axis 101 of the first jaw 140 relative to the second longitudinal axis 103 of the second jaw 150, the length L1 between the first pivot point 132 and the second pivot point 134 is identical to the length L2 between pivot points 146 and 148 on first jaw 140, as shown in FIGS. 7A and 7B. If the length L3 between the second fixed pivot point 134 and 148 on first back link 180 is identical to the length L4 between the first pivot point 132 and the second slide point 146 on first front link 160, then a perfectly parallel mechanism is realized. That is, the longitudinal axis line joining the first pivot point 132 and the second fixed pivot point 134 is perfectly parallel to the longitudinal axis line joining pivot point 146 and 148. The length L6 between pivot point 156 and 158 is identical to the length L1 between the first pivot point 132 and the second pivot point 134, then the longitudinal axis line joining pivot point 156 and 158 is perfectly parallel to the longitudinal axis line joining pivot point 146 and 148. If two lines are parallel to the same line, then they must be parallel to each other. Effectively proving that first jaw 140 is parallel to second jaw 150. In one embodiment, there are two four-bar mechanisms (a special type of parallelogram mechanism), first pivot mechanism comprises of pivots 132, 134, 148, and 146; the second pivot mechanism comprises of pivots 132, 134, 154, and 156.

Figure 6C:
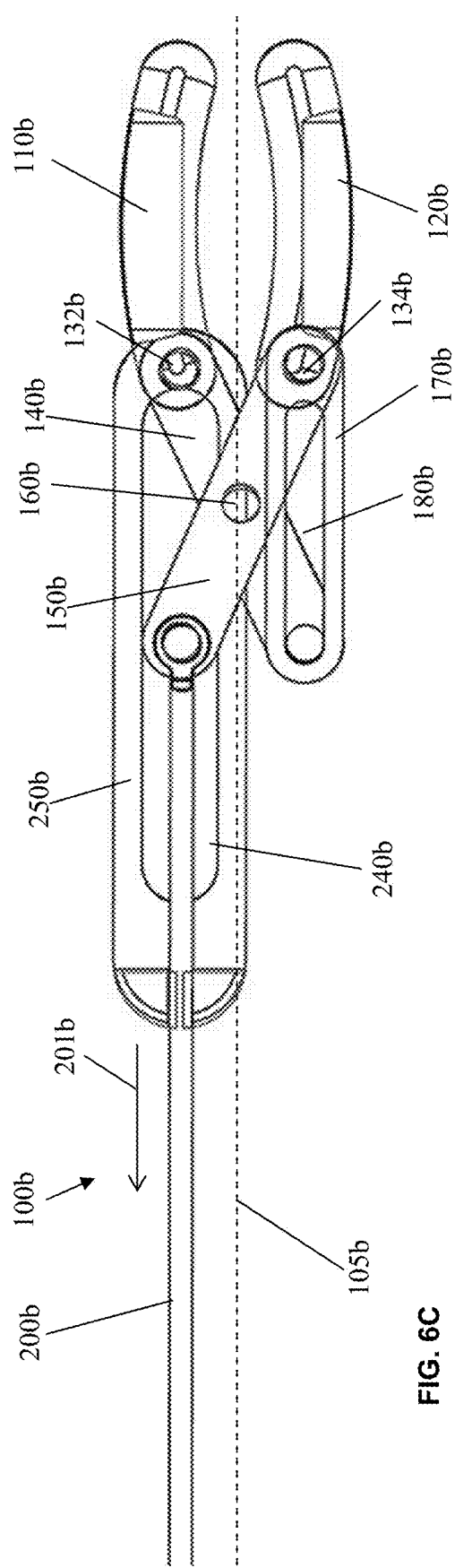
FIG. 6C is a side view of an alternative embodiment surgical forceps in the closed position with the pivot housing shown in phantom according to one embodiment.
Figure 6D:
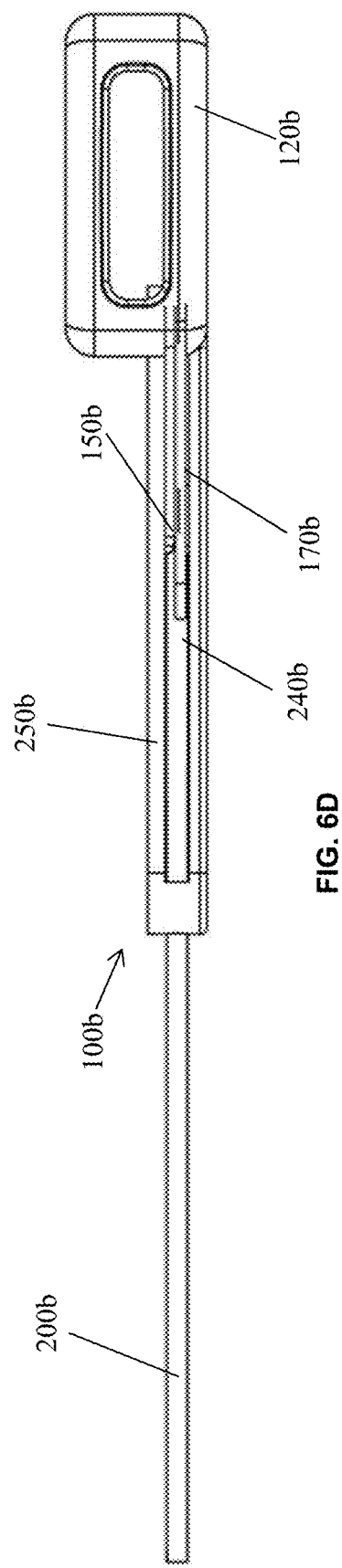
FIG. 6D is a side view of an alternative embodiment surgical forceps in the open position with the pivot housing according to one embodiment.

As shown in FIG. 5B, the three-bar mechanism 130b keeps the open position and the first clamp 110b and the second clamp 120b separated by distance D1b and moves to the closed position where the first clamp 110b and the second clamp 120b are separated by distance D2b, as shown in FIG. 4B. Distance D1b may be between about 1 cm and about 20 cm and distance D2b may be between about 0 cm to about 0.9 cm. The distance D1b and D2b may be altered depending on the type of foreign body being removed. The three-bar mechanism comprises a first fixed point 132b between the first clamp 110b and the first crosslink 140b, and a second fixed point 134b between the second clamp 120b and the second crosslink 150b. The actuator rod 200b moves proximally along the longitudinal axis 105b of the surgical forceps 100b, generally shown by arrow 201b in FIG. 6C. The actuator rod 200b pulls the second crosslink 150b along the longitudinal housing 240b, which then causes the central pivot 160b to pivot about an axis and rotate the first crosslink 140b. The rotation of the first crosslink 140b about the central pivot 160b closes the first clamp 110b while the first crosslink 140b distally moves along the slidable opening 180b. This closing action closes the first clamp 110b and the second clamp 120b into a parallel or nearly parallel closed position, while the first crosslink 140b and the second crosslink 150b maintain the first clamp 110b and the second clamp 120b in a parallel or nearly parallel position during the entire time the actuator rod 200b closes the first fixed point 132b and the second fixed point 134b. FIG. 6D is a side view of the surgical forceps 100b in the open position with the longitudinal housing 240b and pivot housing 250b according to one embodiment.

Figure 7C:
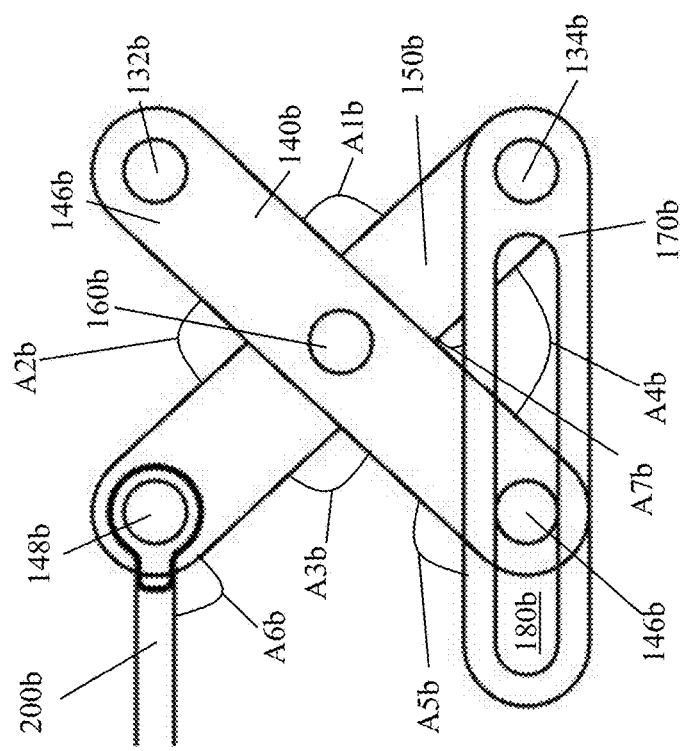
FIG. 7C is a side view of the three-bar mechanism without the pivot housing according one embodiment.

To achieve parallel jaw action of the first clamp and the second clamp, the first longitudinal axis 101b of the first crosslink 140b relative to the second longitudinal axis 103b of the second crosslink 150b is perpendicular, the length L1b between the first fixed point 132b and the second fixed point 134b is identical to the length L2b between first slide point 146b on the first crosslink 140b and second slide point 148b on the second crosslink 150b, as shown in FIG. 7C. If the length L4b between the second fixed point 134b and first slide point 146b is identical to the length L3b between first fixed point 132b and second slide point 148b, then a perfectly parallel mechanism is realized. That is, the longitudinal axis line joining first fixed point 132b and the second slide point 148b is perfectly parallel to the longitudinal axis line joining 134b and 146b. The longitudinal axis of the first clamp 110b is perfectly parallel to the longitudinal axis joining the first fixed point 132*b* and the second slide point 148*b*, and the longitudinal axis of the second clamp 120*b* perfectly parallel to the longitudinal axis line joining 134*d* and 146*b*. If two lines are parallel to the same line, then they must be parallel to each other. Effectively proving that first clamp 110*b* is parallel to the second clamp 120*b*.

The first clamp 110*b* is parallel with respect to the pivot housing 250*b*, and the second clamp 120*b* is parallel with respect to the pivot housing 250*b* during operation. The first crosslink 140*b* pivots with respect to first fixed point 132*b*, where first fixed point 132*b* operates as a pin. The second crosslink 150*b* pivots with respect to second fixed point 134*b*, where second fixed point 134*b* operates as a second pin. The first slide point 146*b* slides with respect to slidable opening 180*b*, where first slide point 146*b* operates as a slide pin. The central pivot 160*b* operates as a central pin between the middle portions of the first crosslink 140*b* and second crosslink 150*b*. The second slide point 148*b* slides within the longitudinal housing 240*b* by way of pin joint and longitudinal movement of the actuator rod 200*b*.

To achieve near parallel jaw action, as shown in FIG. 7B, the length L1 between the first pivot point 132 and the second fixed point 134 is identical to the length L5 between pivot points 146 and 148 on first jaw 140, however, if the length L3 between the second fixed pivot point 134 and 148 on first back link 180 is not identical to the length L4 between 132 and 146 on first front link 160, then a nearly parallel mechanism is realized. That is, the longitudinal axis line joining the first pivot point 132 and the second fixed pivot point 134 is nearly parallel to the longitudinal axis line joining pivot point 146 and 148. The same can be said about the longitudinal axis line joining pivot point 156 and 158 is nearly parallel to the longitudinal axis line joining the first pivot point 132 and the second fixed pivot point 134. If two lines are nearly parallel to the same line, then they must be nearly parallel to each other. Effectively proving that first jaw 140 is nearly parallel to second jaw 150. Note that, there are two four-bar mechanisms first mechanism comprises of pivots 132, 134, 148, and 146; the second mechanism comprises of pivots 132, 134, 154, and 156. To summarize, modifying the length of any of the four links 140, 160, 180 and matching the change on the mirrored links 150, 170, 190 will achieve a general four-bar mechanism with having the first jaw 140 and second jaw 150 being nearly parallel.

As shown in FIG. 7A, the four-bar mechanism 130 comprises the first jaw 140, the second jaw 150, the first front link 160 and the second front link 170, the first back link 180 and the second back link 190, the first linking actuator 210 and the second linking actuator 220, and the actuator rod 200. The first jaw 140 includes a first end 142, a second end 144, and a pivot point 146. The first front link 160 includes a first end 162 and a second end 164, wherein the second end 164 is rotatably coupled with the pivot point 146 of the first jaw 140. The first end 162 is operably coupled with the first pivot point 132. The second front link 170 includes a first end 172 and a second end 174, wherein the second end 174 is operably coupled with the first pivot point 132 and the first end 172 is rotatably coupled with a pivot point 156 on the second jaw 150. The second jaw 150 includes a first end 152 and a second end 154, wherein the pivot point 156 is disposed on the first end 152. The second end 154 of the second jaw 150 includes a second pivot point 158, wherein the second pivot point 158 is operably coupled with the second back link 190. The second back link 190 includes a first end 192 and a second end 194, wherein the second end 194 is rotatably coupled with the second pivot point 158 and the first end 192 is operably coupled with the second fixed pivot point 134. The first back link 180 includes a first end 182 and a second end 184, wherein the second end 184 is operably coupled with the second fixed pivot point 134 and the first end 182 is operably coupled with a second pivot point 148 on the second end 144 of the first jaw 140. The second pivot point 148 is operably coupled with the first linking actuator 210. The first linking actuator 210 includes a first end 212 and a second end 214, wherein the first end 212 is operably coupled with the second pivot point 148 of the first jaw 140 and the second end 214 includes a back pivot point 216. The back pivot point 216 is operably coupled with the second linking actuator 220. The second linking actuator 220 includes a first end 222 and a second end 224, wherein the first end 222 is operably coupled with the second pivot point 158 of the second jaw 150, and the second end 224 is operably coupled with the back pivot point 216. The back pivot point 216 is further coupled with the actuator rod 200. As indicated previously, the proximal longitudinal movement of the actuator rod 200 pivots the four-bar mechanism 130.

As shown in FIG. 7B, the first jaw 140 makes an angle A1 with the first front link 160, the first front link 160 makes an angle A3 with the second front link 170, the second front link 170 makes an angle A2 with the second jaw 150, the second jaw 150 makes an angle A5 with the second back link 190, the second back link 190 makes an angle A6 with the first back link 180, the first back link 180 makes an angle A4 with the first jaw 140, the first back link 180 makes an angle A7 with the first linking actuator 210, the first linking actuator makes an angle A9 with the second linking actuator 220, and the second linking actuator 220 makes an angle A8 with the second back link 190. In the open position, the angle A1 is greater than about 90 degrees, the angle A3 is greater than about 180 degrees, the angle A2 is greater than about 90 degrees, the angle A4 is greater than about 45 degrees, the angle A5 is greater than about 45 degrees, the angle A6 is greater than about 180 degrees, the angle A7 is less than about 45 degrees, the angle A8 is less than about 45 degrees, and the angle A9 is about 45 degrees. Upon proximal longitudinal movement of the actuator rod 200 to the closed position, the angle A1 pivots from pivot point 146 to be less than about 20 degrees, the angle A2 pivots from pivot point 156 to be less than about 20 degrees, the angle A3 pivots from first pivot point 132 to be less than about 20 degrees, the angle A4 pivots about second pivot point 148 to be less than about 20 degrees, the angle A5 pivots about second pivot point 158 to be less than about 20 degrees, the angle A6 pivots about the second fixed pivot point 134 to be less than about 20 degrees, the angle A7 pivots about second pivot point 148 to be less than about 20 degrees, the angle A8 pivots about second pivot point 158 to be less than about 20 degrees, the angle A9 pivots about the back pivot point 216 to be less than about 10 degrees. The four-bar mechanism 130 translates and pivots about in the pivot housing 240.

Figure 7D:
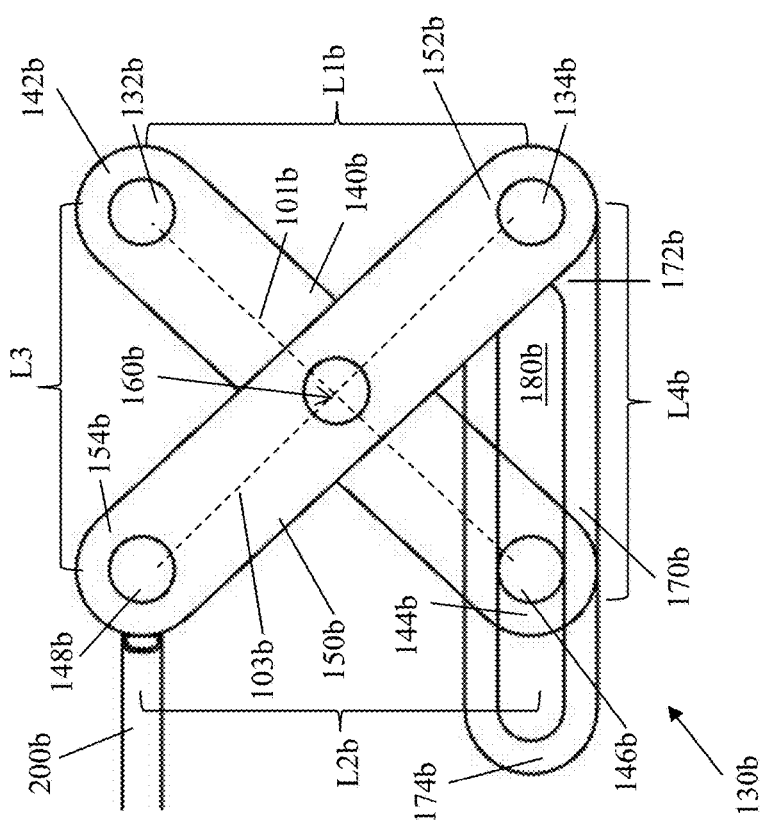
FIG. 7D is a side view of the three-bar mechanism showing the angles $A1b$-$A6b$ without the pivot housing according one embodiment.

To achieve near parallel jaw action in surgical forceps 100*b*, as shown in FIG. 7D, the length L1*b* between the first fixed point 132*b* and second fixed point 134*b* is identical to the length L2*b* between first slide point 146*b* and second slide point 148*b*, however, if the length L3*b* between the first fixed point 132*b* and second slide point 148*b* is not identical to the length L4*b* between 134*b* and 146*b*, then a nearly parallel mechanism is realized. That is, the longitudinal axis line joining the first fixed point 132*b* and the second slide point 148*b* is nearly parallel to the longitudinal axis line joining first slide point 146*b* and the second fixed point 134*b*. If two lines are nearly parallel to the same line, then they must be nearly parallel to each other. Effectively proving that first clamp 110b is nearly parallel to second clamp 120b.

As shown in FIG. 7C, the three-bar mechanism 130b comprises the first crosslink 140b, the second crosslink 150b, the pivot link 170b, and the actuator rod 200b. The first crosslink 140b includes a first end 142b, a second end 144b, and the central pivot 160b. The second crosslink 150b includes a first end 152b, a second end 154b, and the central pivot 160b, wherein the first crosslink 140b and the second crosslink 150b are rotatably coupled with the central pivot 160b. The pivot link 170b includes a first end 172b, a second end 174b, and the slidable opening 180b, wherein the slidable opening 180b is operably disposed between the first end 172b and the second end 174b. The second end 174b is operably coupled with the first slide point 146b and the first end 172b is rotatably coupled with a second fixed point 134b on the second crosslink 150b. The second fixed point 134b is disposed on the first end 152b of the second crosslink 150b, and the first end 152b is operably coupled with the first end 172b of the pivot link 170b. The second end 154b of the second crosslink 150b includes the second slide point 148b, wherein the second slide point 148b is operably coupled with the actuator rod 200b. The second slide point 148b is further coupled with the actuator rod 200b. As indicated previously, the proximal longitudinal movement of the actuator rod 200b pivots the three-bar mechanism 130b about central pivot 160b.

As shown in FIG. 7D, the first crosslink 140b makes an angle A1b with the second crosslink 150b between the first fixed point 132b and the second fixed point 134b, the first crosslink 140b makes an angle A2b with the second crosslink 150b between first fixed point 132b and the second slide point 148b, the first crosslink 140b makes an angle A3b with the second crosslink 150b between first slide point 146b and second slide point 148b, the first crosslink 140b makes an angle A4b with the second crosslink 150b between first slide point 146b and second fixed point 134b, the first crosslink 140b makes an angle A5b with the pivot link 170b, the second crosslink 150b makes an angle A6b with the actuator rod 200b, and the second crosslink 150b makes an angle A7b with the pivot link 170b. In the open position, the angle A1b is equal to angle A2b, A3b, and A4b is about 90 degrees. The angle A5b is greater than about 90 degrees, the angle A6b is greater than about 90 degrees, and the angle A7b is less than about 45 degrees. Upon proximal longitudinal movement of the actuator rod 200b to the closed position, the angle A1b pivots about central pivot 160b to be less than about 90 degrees, the angle A2b pivots about central pivot 160b to be greater than about 90 degrees, the angle A3b pivots about central pivot 160b to be less than about 90 degrees, the angle A4b pivots about central pivot 160b to be greater than about 90 degrees, the angle A5b pivots the second end 174b of the second front link 170b to be greater than about 120 degrees, the angle A6b pivots about the second slide point 148b to be greater than about 120 degrees, the angle A1b pivots about second fixed point 134b to be less than about 10 degrees. The three-bar mechanism 130b translates and pivots about in the pivot housing 250b.

Figure 9A:
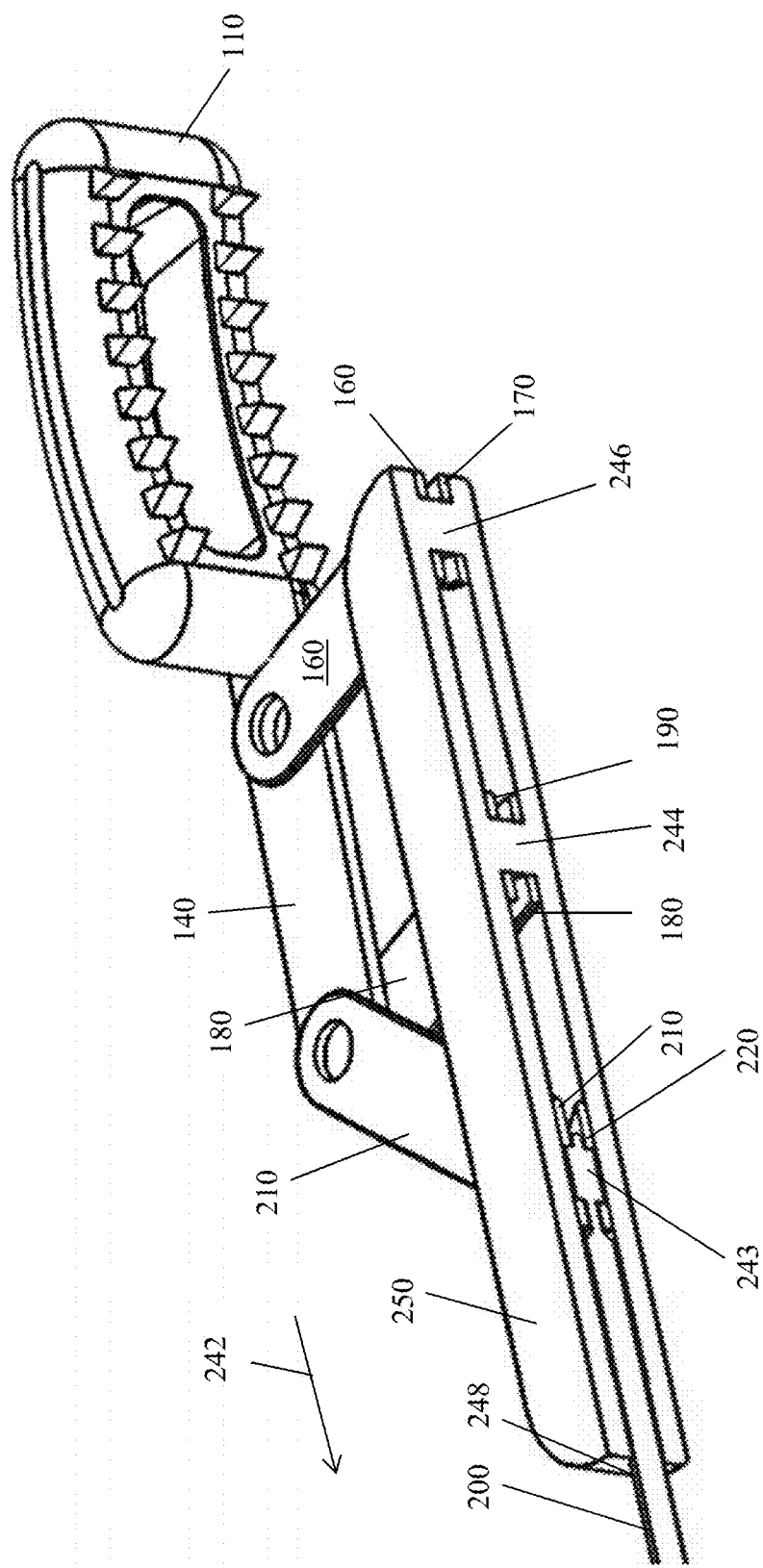
FIG. 9A is a perspective cross sectional view of the pivot housing and the four-bar mechanism coupled with the actuator rod according to one embodiment.

As shown in FIGS. 8A-8C, the pivot housing 240 includes a distal end 241, a proximal end 243, and a pivot lumen 242 in which the four-bar mechanism 130 is operably disposed. The pivot lumen 242 includes a middle pivot pin 244 and a distal pivot pin 246. The middle pivot pin 244 operably couples with the second fixed pivot point 134 and the distal pivot pin 246 operably couples with the first pivot point 132, as shown in FIG. 9A. The first pivot point 132 rotates about the distal pivot pin 246, generally shown by arrow P1 in FIG. 8B. The second fixed pivot point 134 rotates about middle pivot pin 244, generally shown by arrow P2 in FIG. 8B. The pivot lumen 242 includes a thickness Tp and the distal pivot pin 246 and the middle pivot pin 244 include a thickness that is equal to thickness Tp as to secure the first pivot point 132 and the second fixed pivot point 134. The thickness Tp of the pivot lumen 242 also permits the four-bar mechanism 130 to rotatably move there within. The pivot housing 240 includes a top portion 245 on which the central tube 250 is operably disposed, as shown in FIG. 6B. The proximal end 243 includes a distal opening 248. The actuator rod 200 is operably disposed through the distal opening 248, as shown in FIG. 9A. The distal opening 248 is sized as to permit the longitudinal movement of the actuator rod 200, generally shown by arrow 247.

Figure 9C:
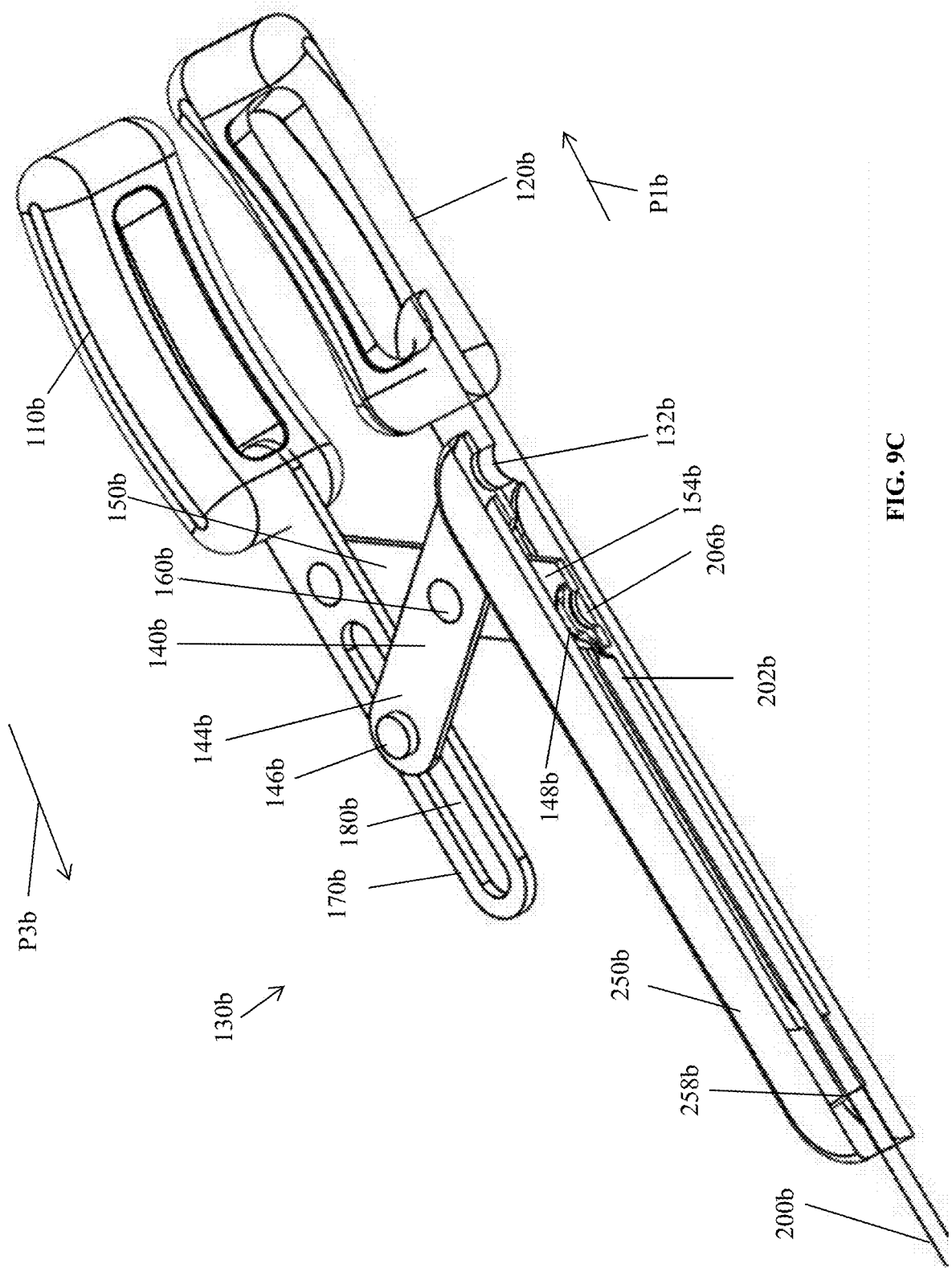
FIG. 9C is a perspective cross sectional view of the pivot housing and the three-bar mechanism coupled with the actuator rod according to one embodiment.

As shown in FIGS. 8D-8F, the pivot housing 250b includes a distal end 251b, a proximal end 253b, and a pivot lumen 252b in which the three-bar mechanism 130b is operably disposed. The pivot lumen 252b includes a distal pivot pin 256b and the longitudinal housing 240b. The longitudinal housing 240b operably couples with the second slide point 148b and the distal pivot pin 256b operably couples with the first fixed point 132b, as shown in FIG. 9C. The first fixed point 132b holds the first clamp 110b in a fixed horizontal position, generally shown by arrow P1b in FIG. 9C. The second slide point 148b longitudinally slides along the pivot lumen 252b, generally shown by arrow P2b in FIG. 8E. The longitudinal housing 240b includes a height Hb and a thickness Th to permit the second slide point 148b to longitudinally traverse the longitudinal housing 240b. The longitudinal housing 240b is disposed within the side portions 255b of the pivot housing 250b, as shown in FIG. 8D. The distal pivot pin 256b include a thickness that is equal to thickness of the first fixed point 132b as to secure the first end 142b of the first crosslink 140b and the first clamp 110b. The proximal end 253b includes a distal opening 258b. The actuator rod 200b is operably disposed through the distal opening 258b, as shown in FIG. 9C. The distal opening 248 is sized as to permit the longitudinal movement of the actuator rod 200b through the longitudinal housing 240b, generally shown by arrow 257b.

Figure 10A:
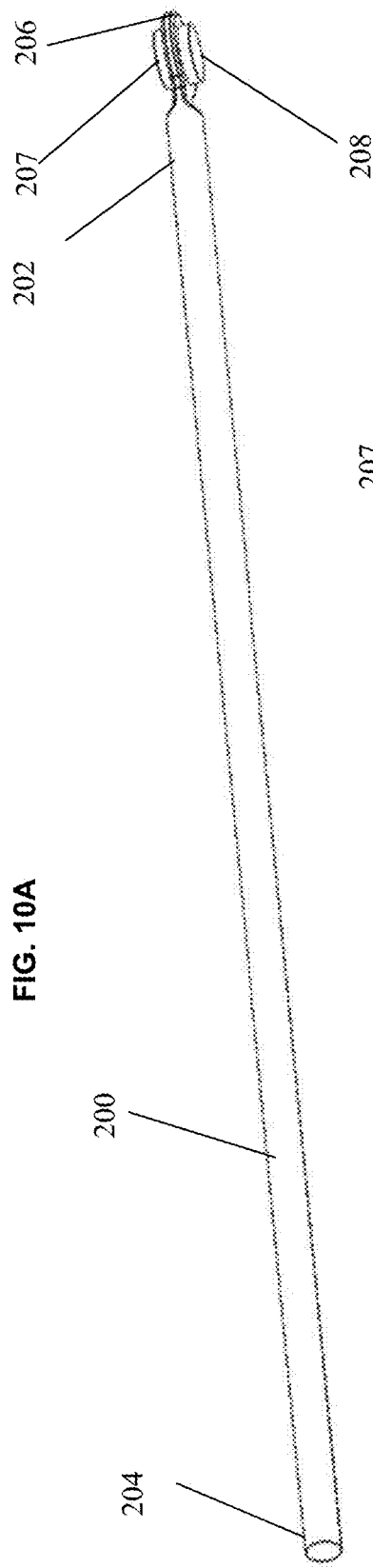
FIG. 10A is a perspective view of the actuator rod according to one embodiment.
Figure 10B:
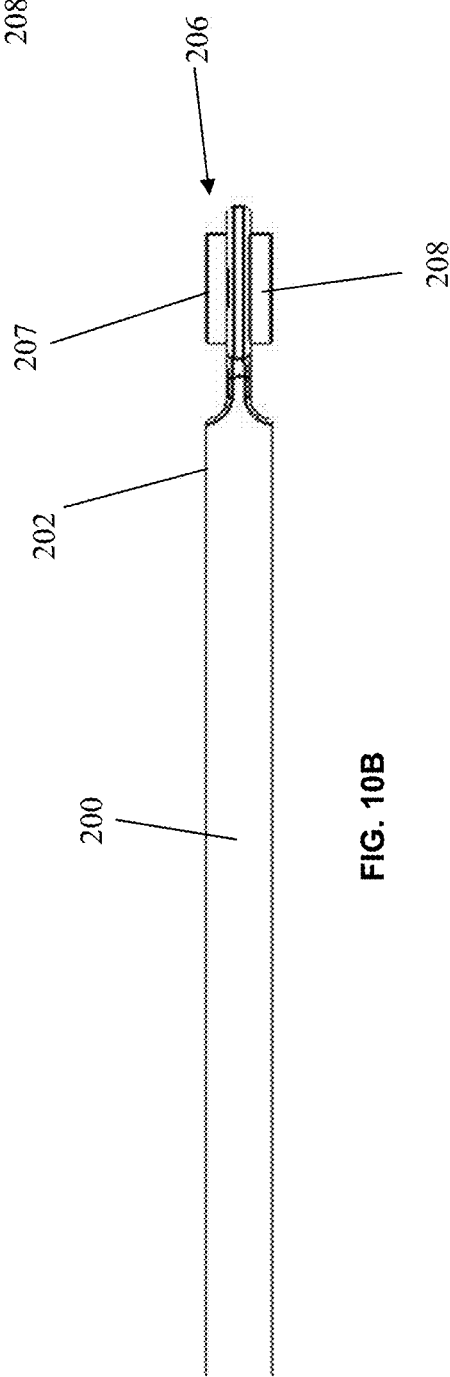
FIG. 10B is a side view of the actuator rod according to one embodiment.
Figure 11A:
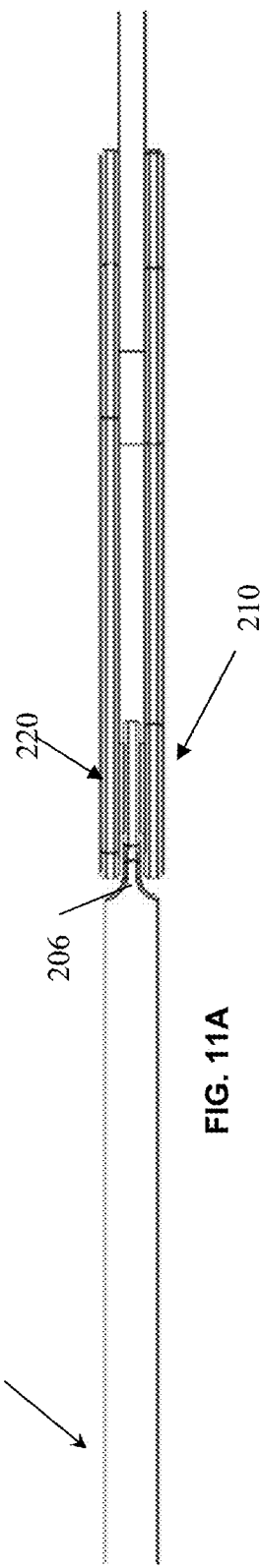
FIG. 11A is a side view of the actuator rod coupled to the first linking actuator and the second linking actuator.

As shown in FIG. 9B and FIG. 10A, the actuator rod 200 is operably coupled with the four-bar mechanism 130. The actuator rod 200 includes a distal end 202 and a proximal end 204, wherein the distal end 202 includes a distal pivot pin 206. The distal pivot pin 206 is further shown in FIG. 10A. The distal pivot pin 206 includes a top portion 207 and a bottom portion 208, as shown in FIG. 10B. The distal pivot pin 206 includes a general circular configuration. The top portion 207 is operably coupled with the second end 214 of the first linking actuator 210 and the bottom portion 208 is operably coupled with the second end 224 of the second linking actuator 220, in one embodiment, as shown in FIG. 11A. Alternatively, the top portion 207 is operably coupled with the second end 224 of the second linking actuator 220 and the bottom portion 208 is operably coupled with the second end 216 of the first linking actuator 210, in another embodiment. The general circular configuration of the distal pivot pin 206 allows the first linking actuator 210 and second linking actuator 220 to rotate about the back pivot point 216 during operation. In one embodiment, the top portion 207 includes a thickness T1 and the bottom portion includes a thickness T2. The first linking actuator 210 and the second linking actuator 220 include a thickness T3 and T4, respectively, which are equal to the thickness T1 and T2 of the top portion 207 and the bottom portion 208.

As shown in FIG. 9C and FIG. 10C, the actuator rod 200*b* is operably coupled with the three-bar mechanism 130*b*. The actuator rod 200*b* includes a distal end 202*b* and a proximal end 204*b*, wherein the distal end 202*b* includes a distal pivot pin 206*b*. The distal pivot pin 206*b* is further shown in FIG. 10C. The distal pivot pin 206*b* includes a top portion 207*b* and a bottom portion 208*b*, as shown in FIG. 10D. The distal pivot pin 206*b* includes a general circular configuration. The top portion 207*b* is operably coupled with the longitudinal housing 240*b* and the bottom portion 208*b* is operably coupled with the second end 154*b* of the second crosslink 150*b*, in one embodiment, as shown in FIG. 11C. Alternatively, the top portion 207*b* is operably coupled with the second end 154*b* of the second crosslink 150*b* and the bottom portion 208*b* is operably coupled with the longitudinal housing 240*b*, in another embodiment. The general circular configuration of the distal pivot pin 206*b* allows the second end 154*b* to slide along the longitudinal housing 240*b* to rotate the second crosslink 150*b* about the central pivot 160*b* during operation. In one embodiment, the top portion 207*b* includes a thickness T1*b* and the bottom portion 208*b* includes a thickness T2*b*. The second crosslink 150*b* includes a thickness T3*b* which is equal or less than the thickness T1*b* of the top portion 207*b*. The bottom portion 208*b* thickness T2*b* is sufficient to engage and slide along longitudinal housing 240*b*.

As shown in FIG. 11B, the actuator rod 200 is operably coupled with the pivot housing 240 and the central tube 250. As shown in FIGS. 12A-12B, the central tube includes a distal end 251 and a proximal end 252. The proximal end 252 includes the opening 124 extending from the proximal end 252 to the middle portion 255 of the central tube 250 and the distal end 251 includes a curved profile for seating a camera or other imaging device. On the bottom portion 256 of the central tube 250, a bottom lumen 254 is disposed for coupling the actuator rod 200. The bottom lumen 254 includes a circumference to permit the longitudinal movement of the actuator rod 200. The pivot housing 240 sits on the bottom portion 256 of the central tube 250 and against the distal end 257 of the bottom lumen 254. The distal opening 248 of the pivot housing 240 is coaxially aligned with the distal end 257 of the bottom lumen 254 to permit seamless longitudinal movement of the actuator rod 200 there between.

As shown in FIGS. 9D and 11C, the actuator rod 200*b* is operably coupled with the pivot housing 250*b*. The distal opening 258*b* of the pivot housing 250*b* is coaxially aligned with the distal end of the actuator rod 200*b* to permit seamless longitudinal movement of the actuator rod 200 there between.

As shown in FIGS. 9C-9D, the pivot link 170*b* includes a second end 174*b* and a first end 172*b* and the slidable opening 180*b* between the second end 174*b* and the first end 172*b*. The second end 144*b* of first crosslink 140*b* includes a circular configuration to engage the slidable opening 180*b* and form the first slide point 146*b*. When the actuator rod 200*b* is longitudinally moved proximally, the second end 144*b* of the first crosslink 140*b* moves in direction P3*b*, shown in FIG. 9C, and causes the first crosslink 140*b* to rotate about central pivot 160*b* and close the first clamp 110*b* and the second clamp 120*b*. When the actuator rod 200*b* is longitudinally moved distally, the second end 144*b* of the first crosslink 140*b* moves in direction P4*b*, shown in FIG. 9D, and causes the first crosslink 140*b* to rotate about central pivot 160*b* and open the first clamp 110*b* and the second clamp 120*b*. The first crosslink 140*b* holds the first clamp 110*b* in the fixed horizontal position during opening and closing of the surgical forceps.

As shown in FIG. 13A, the first jaw 140 includes the first end 142, the second end 144, with a distal opening 141 on the first end 142 and a proximal pin 143 disposed on the bottom portion 145 of the second end 144. The proximal pin 143 operates the second pivot point 148 and rotatably couples the first linking actuator 210 and the second front link 180 as shown in FIG. 13B. The second jaw 150 is shown in FIG. 13C and includes the first end 152, the second end 154, with a distal opening 151 on the first end 152 and a proximal pin 153 disposed on the top portion 155 of the second end 154. The proximal pin 153 operates the second pivot point 158 and rotatably couples the second linking actuator 220 and the second back link 190. The first end 142 of the first jaw 140 include a connection portion 149 to attach the first clamp 110 and the first end 152 of the second jaw 150 include a connection portion 159 to attach the second clamp 120.

As shown in FIGS. 14A-14C, the first clamp 110 is generally shown and is identical to the second clamp 120. The first clamp 110 includes a first end 111 and a second end 112 with a first gripping portion 118 extending from the first end 111 to the second end 112. Either the first end 111 or the second end 112 is operably attached to the first jaw 140. The first gripping portion 118 is operably disposed on the bottom portion 113 of the first clamp 110. The first gripping portion 118 may comprise a plurality of teeth 114, or alternatively, the first gripping portion 118 may include a textured surface or other gripping elements to secure and grip a foreign body. The first gripping portion 118 includes a length L8 which is sufficient to secure a foreign body and may be adjustable. The plurality of teeth 114 may include a height H1 from the bottom portion 113, which is sufficient to secure a foreign body and may be adjusted accordingly. In one embodiment, the bottom portion 113 includes a general curved cross sectional profile, which thereby imparts a curved cross sectional profile for the first gripping portion 118. In one embodiment, the first clamp 110 includes a central opening 115 extending from the first end 111 and the second end 112. The central opening 115 may be configured to permit the foreign body to extend through the central opening 115 when the four-bar mechanism is in the closed position. This may prevent any kinking or deterrence of the four-bar mechanism from closing if the foreign body is larger than the closed position of the four-bar mechanism.

Figure 15:
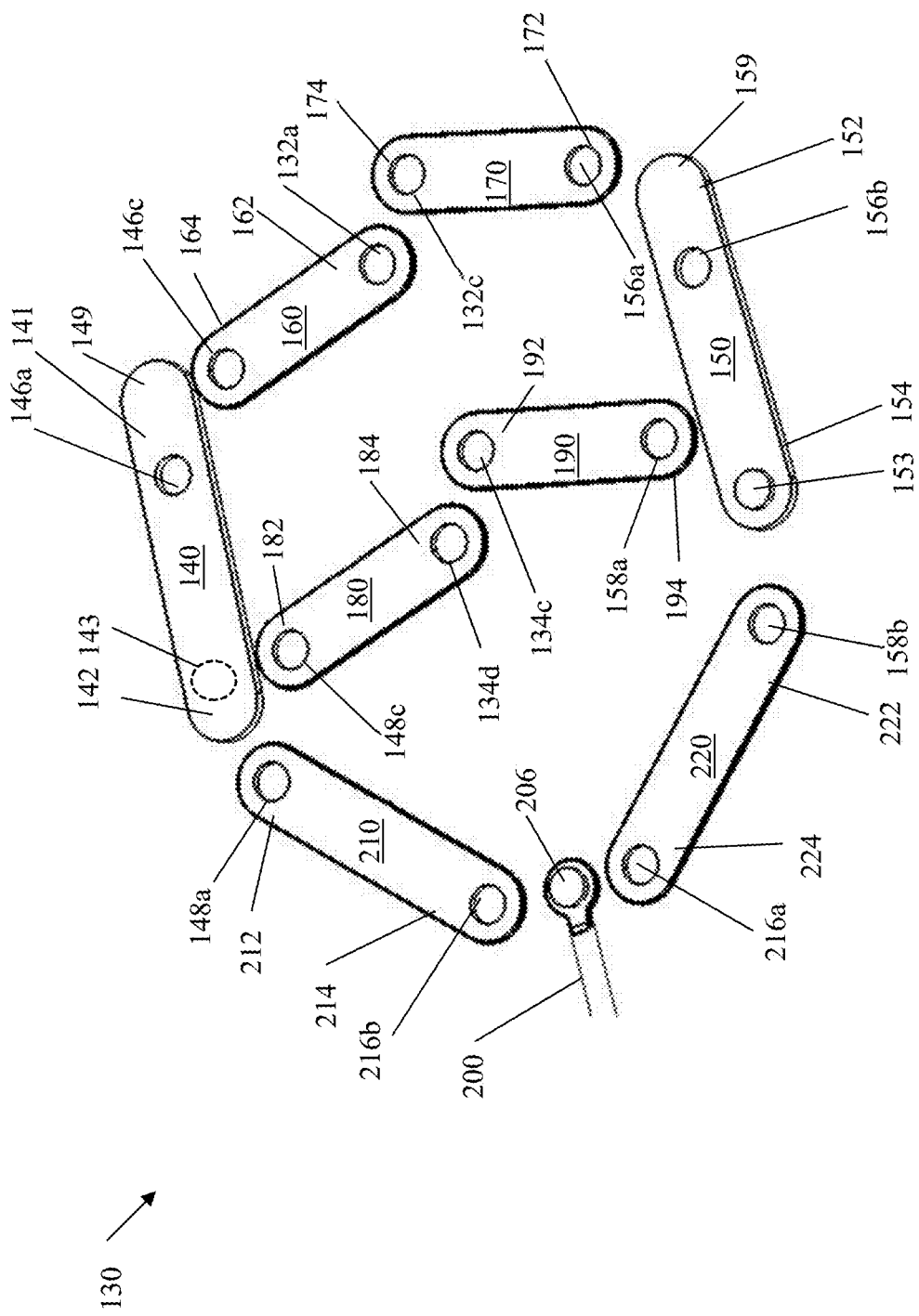
FIG. 15 is a perspective exploded view of the four-bar mechanism.

As shown in FIG. 15, the first jaw 140 includes the first end 142, the second end 144, and a first pivot point 146*a* disposed on the first end 142. The first pivot point 146*a* is a generally circular opening operably coupled with a second pivot point 146*c* on the second end 164 of the first front link 160. The second pivot point 146*c* is a generally circular opening matched to the first pivot point 146*a*. The first pivot point 146*a* coaxially aligns with the second pivot point 146*c* to permit rotational movement of the first front link 160 relative to the first jaw 140, which remains in a parallel or nearly parallel position during the transition from the open to closed position. The first end 162 of the first front link 160 includes a first pivot point 132*a* that coaxially aligns with a second pivot point 132*c* on the second end 174 of the second front link 170. The first pivot point 132*a* and the second pivot point 132*c* include a matched generally circular opening. The first pivot point 132*a*, the second pivot point 132*c*, and the first pivot point 132 coaxially align to permit rotational movement of the first front link 160 and the second front link 170, which decreases angle A3 during the transition from the open to closed position.

The first end 172 of the second front link 170 includes a first pivot point 156a that coaxially aligns with a second pivot point 156b on the first end 152 of the second jaw 150. The first pivot point 156a and the second pivot point 156b include a matched generally circular opening. The first pivot point 156a coaxially aligns with the second pivot point 156b to permit rotational movement of the second front link 170 relative to the second jaw 150, which remains in a parallel or nearly parallel position during the transition from the open to closed position.

As shown in FIG. 15, the second end 154 of the second jaw 150 includes the proximal pin 153 rotatably coupled with a first pivot point 158a on the second end 194 of the second back link 190 and a second pivot point 158b on the first end 222 of the second linking actuator 220. The first pivot point 158a and the second pivot point 158b include a matched generally circular opening to the proximal pin 153. The first pivot point 158a coaxially aligns with the second pivot point 158b and the proximal pin 153 to permit rotational movement of the second back link 190 relative to the second jaw 150 to decrease angle A5 during the transition from the open to closed position, and rotational movement of the second linking actuator 220 relative to the second back link 190 to decrease angle A8 during the transition from the open to closed position.

The second back link 190 includes a second pivot point 134c on the first end 192, wherein the second pivot point 134c is rotatably coupled with a first pivot point 134a on the second end 184 of the first back link 180. The first pivot point 134a and the second pivot point 134c include a matched generally circular opening. The first pivot point 134a coaxially aligns with the second pivot point 134c to permit rotational movement of the second back link 190 relative to the first back link 180, which closes angle A6 position during the transition from the open to closed position.

The first back link 180 includes a second pivot point 148c on the first end 182, wherein the second end 144 of the first jaw 140 includes the proximal pin 143 and the first end 212 of the first linking actuator 210 includes a first pivot point 148a. The first pivot point 148a and the second pivot point 148c coaxially align with the proximal pin 143. The first pivot point 148a and the second pivot point 148c include a matched generally circular opening to the proximal pin 143. The first pivot point 148a coaxially aligns with the second pivot point 148c and the proximal pin 143 to permit rotational movement of the first back link 180 relative to the first jaw 140 to decrease angle A4 during the transition from the open to closed position, and rotational movement of the first linking actuator 210 relative to the first back link 180 to decrease angle A7 during the transition from the open to closed position.

The first linking actuator 210 includes a second pivot point 216b on the second end 214, wherein the second end 224 of the second linking actuator 220 includes a first pivot point 216a. The second pivot point 216b and the first pivot point 216a are coaxially coupled with the distal pivot pin 206 on either the top portion 207 or bottom portion 208. The first pivot point 216a and the second pivot point 216b include a matched generally circular opening to the distal pivot pin 206. The first pivot point 216a coaxially aligns with the second pivot point 216b and the distal pivot pin 206 to permit rotational movement of the first linking actuator 210 relative to the second linking actuator 220 to decrease angle A9 during the transition from the open to closed position when the actuator rod 200 is longitudinally moved towards the proximal end of the surgical forceps.

As can be understood by one skilled in the art, the surgical forceps 100 and/or any of its components may have any size, shape, length, thickness, height, weight, or any other parameters. Such parameters may be selected by the surgeon (or other qualified professional) for performance of specific procedures. Further, the surgical forceps and/or any of its components may be manufactured from metal, plastic, synthetic material, or other suitable materials, or any combination thereof. In one embodiment, the surgical forceps 100 is composed of a metal alloy, titanium, nitinol, or stainless steel, or alternatively, any medical grade composite or ceramic.

In some embodiments, various lengths and configurations may also include various features to accommodate different applications for the surgical forceps. The surgical forceps can be constructed of various materials to aid in radio translucency, strength, flexibility, and integration with anatomy, etc.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A surgical forceps comprising: a first clamp and a second clamp operably coupled to a four-bar mechanism to move the first clamp and the second clamp from an open position to a closed position; the four-bar mechanism includes a first jaw operably coupled to the first clamp and a second jaw operably coupled to the second clamp; the first clamp includes a first gripping portion and the second clamp includes a second gripping portion in which to grip a foreign body when the surgical forceps are in a parallel closed position; the first jaw is operably attached to a first front link and a first back link, and the second jaw is operably attached to a second front link and a second back link; the first jaw and second jaw are operably coupled to an actuator rod which moves the first jaw and the second jaw through a first linking actuator and a second linking actuator by a double pivot action; a central tube is operably coupled to the actuator rod and holds a pivot housing to maintain and house the four-bar mechanism; and the central tube includes an opening through which a camera or viewing mechanism is coaxially disposed for viewing a distal end of the surgical forceps.

2. The surgical forceps of claim 1, wherein the first jaw includes a first longitudinal axis and the second jaw includes a second longitudinal axis, and the four-bar mechanism keeps the first longitudinal axis of the first jaw parallel or nearly parallel relative to the second longitudinal axis of the second jaw.

3. The surgical forceps of claim 2, wherein the four-bar mechanism keeps the open position and the first clamp and the second clamp separated by distance D1 and moves to the closed position where the first clamp 110 and the second clamp 120 are separated by a distance D2, wherein distance D1 may be between about 1 cm and about 20 cm and the distance D2 may be between about 0 cm to about 0.9 cm.

4. The surgical forceps of claim 3, wherein the actuator rod moves proximally along a longitudinal axis of the surgical forceps and the actuator rod pulls the first linking actuator and the second linking actuator which then causes a first fixed pivot point and a second fixed pivot point to pivot; and the first fixed pivot point closes the first front link and the second front link while the second fixed pivot point closes the first back link and the second back link which closes the first clamp and the second clamp into the parallel or nearly parallel closed position, while the first jaw and the second jaw maintain the first clamp and the second clamp in a nearly parallel position during the transition from the open position to the closed position, and the actuator rod closes the first fixed pivot point and the second fixed pivot point.

5. The surgical forceps of claim 4, wherein the first jaw includes a first end, a second end, and a pivot point; the first front link includes a first end and a second end, wherein the second end is rotatably coupled with the pivot point of the first jaw; the first end is operably coupled with the first fixed pivot point; the second front link includes a first end and a second end, wherein the second end of the second front link is operably coupled with the first fixed pivot point and the first end of the second front link is rotatably coupled with a pivot point on the second jaw; the second jaw includes a first end and a second end, wherein the pivot point is disposed on the first end of the second jaw; the second end of the second jaw includes a second pivot point, wherein the second pivot point is operably coupled with the second back link; the second back link includes a first end and a second end, wherein the second end of the second back link is rotatably coupled with the second pivot point and the first end of the second back link is operably coupled with the second fixed pivot point; the first back link includes a first end and a second end, wherein the second end of the first back link is operably coupled with the second fixed pivot point and the first end of the first back link is operably coupled with a second pivot point on the second end of the first jaw; the second pivot point is operably coupled with the first linking actuator; the first linking actuator includes a first end and a second end, wherein the first end of the first linking actuator is operably coupled with the second pivot point of the first jaw and the second end of the first linking actuator includes a back pivot point; and the back pivot point is operably coupled with the second linking actuator; the second linking actuator includes a first end and a second end, wherein the first end of the second linking actuator is operably coupled with the second pivot point of the second jaw, and the second end of the second linking actuator is operably coupled with the back pivot point; the back pivot point is coupled with the actuator rod.

* * * * *